(12) United States Patent
DeAngelis et al.

(10) Patent No.: US 10,071,282 B2
(45) Date of Patent: *Sep. 11, 2018

(54) ASSOCIATIVE OBJECT TRACKING SYSTEMS AND METHODS

(71) Applicant: Isolynx, LLC, Haverhill, MA (US)

(72) Inventors: Douglas J. DeAngelis, Ipswich, MA (US); Edward G. Evansen, West Newbury, MA (US); Gerard M. Reilly, Newton, MA (US)

(73) Assignee: ISOLYNX, LLC, Haverhill, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,880

(22) Filed: Oct. 20, 2017

(65) Prior Publication Data

US 2018/0036590 A1 Feb. 8, 2018

Related U.S. Application Data

(63) Continuation of application No. 15/163,242, filed on May 24, 2016, now Pat. No. 9,795,830, which is a
(Continued)

(51) Int. Cl.
*A63B 24/00* (2006.01)
*A61B 5/145* (2006.01)
(Continued)

(52) U.S. Cl.
CPC ...... *A63B 24/0021* (2013.01); *A61B 5/02438* (2013.01); *A61B 5/0816* (2013.01);
(Continued)

(58) Field of Classification Search
CPC ............ A63B 24/0021; A63B 24/0062; A63B 71/00619; A63B 71/00622;
(Continued)

(56) References Cited

U.S. PATENT DOCUMENTS

| | | | |
|---|---|---|---|
| 4,980,871 A | 12/1990 | Sieber et al. | |
| 5,373,319 A | 12/1994 | Lee | |

(Continued)

FOREIGN PATENT DOCUMENTS

| | | |
|---|---|---|
| WO | 1998/005977 A1 | 2/1998 |
| WO | 2001/008417 A1 | 2/2001 |
| WO | 2014/197600 A1 | 12/2014 |

OTHER PUBLICATIONS

Australian Patent Application No. 2011329607 Examination Report dated Sep. 15, 2014, 3 pages.

(Continued)

*Primary Examiner* — Sisay Yacob
(74) *Attorney, Agent, or Firm* — Lathrop Gage LLP

(57) ABSTRACT

Systems and methods track a first object when continuous tracking information for the first object is not available. The systems and methods detect when the tracking information for the first object is not available. A last time of a last determined location of the first object is determined and a second object closest to the last determined location at the last time is determined. The location of the first object is associated with a location of the second object if tracking information for the first object is not available.

14 Claims, 13 Drawing Sheets

Related U.S. Application Data continuation of application No. 13/301,614, filed on Nov. 21, 2011, now Pat. No. 9,375,628.

(60) Provisional application No. 61/415,707, filed on Nov. 19, 2010.

(51) Int. Cl.

| | | |
|---|---|---|
| *A61B 5/08* | (2006.01) | |
| *A63B 71/06* | (2006.01) | |
| *A61B 5/024* | (2006.01) | |
| *G06T 7/20* | (2017.01) | |
| *G06K 9/00* | (2006.01) | |
| *G06Q 50/28* | (2012.01) | |
| *G06Q 10/08* | (2012.01) | |
| *A63B 102/22* | (2015.01) | |
| *G01S 13/75* | (2006.01) | |
| *G01S 13/72* | (2006.01) | |

(52) U.S. Cl.
CPC ...... *A61B 5/14542* (2013.01); *A63B 24/0062* (2013.01); *A63B 71/0619* (2013.01); *A63B 71/0622* (2013.01); *G06K 9/00751* (2013.01); *G06Q 10/0833* (2013.01); *G06Q 50/28* (2013.01); *G06T 7/20* (2013.01); *A61B 2503/10* (2013.01); *A63B 2024/0025* (2013.01); *A63B 2024/0028* (2013.01); *A63B 2071/0625* (2013.01); *A63B 2102/22* (2015.10); *A63B 2220/14* (2013.01); *A63B 2220/836* (2013.01); *A63B 2225/15* (2013.01); *A63B 2225/20* (2013.01); *A63B 2243/0037* (2013.01); *G01S 13/726* (2013.01); *G01S 13/751* (2013.01); *G06T 2207/10016* (2013.01); *G06T 2207/30221* (2013.01)

(58) Field of Classification Search
CPC ........ A63B 2102/22; A63B 2024/0025; A63B 2024/0028; A63B 2071/0625; A63B 2220/14; A63B 2220/836; A63B 2225/15; A63B 2225/20; A63B 2243/0037; A61B 5/02438; A61B 5/0816; A61B 5/14542; A61B 2503/10; G06K 9/00751; G06Q 10/0833; G06Q 50/28; G06T 7/20; G06T 2207/10016; G06T 2207/30221; G01S 13/726; G01S 13/751

See application file for complete search history.

(56) References Cited

U.S. PATENT DOCUMENTS

| | | | |
|---|---|---|---|
| 5,465,144 | A | 11/1995 | Parker et al. |
| 5,920,288 | A | 7/1999 | Sorrells |
| 6,204,813 | B1 | 3/2001 | Wadell et al. |
| 6,661,342 | B2 | 12/2003 | Hall et al. |
| 6,710,713 | B1 | 3/2004 | Russo |
| 6,882,315 | B2 | 4/2005 | Richley et al. |
| 6,998,987 | B2 | 2/2006 | Lin |
| 7,511,604 | B2 | 3/2009 | Raphaeli et al. |
| 7,667,604 | B2 | 2/2010 | Ebert et al. |
| 7,671,802 | B2 | 3/2010 | Walsh et al. |
| 7,710,322 | B1 | 5/2010 | Ameti et al. |
| 7,969,348 | B2 | 6/2011 | Baker et al. |
| 8,169,319 | B2 | 5/2012 | Kaplan et al. |
| 8,289,185 | B2 | 10/2012 | Alonso |
| 8,457,392 | B2 | 6/2013 | Cavallaro et al. |
| 8,477,046 | B2 | 7/2013 | Alonso |
| 8,705,671 | B2 | 4/2014 | Ameti et al. |
| 8,768,343 | B2 | 7/2014 | Wisherd |
| 8,786,495 | B2 | 7/2014 | Wisherd et al. |
| 8,842,002 | B2 | 9/2014 | Rado |
| 2002/0022490 | A1 | 2/2002 | Usui |
| 2002/0041284 | A1 | 4/2002 | Konishi et al. |
| 2002/0116147 | A1 | 8/2002 | Vock et al. |
| 2003/0095186 | A1 | 5/2003 | Aman et al. |
| 2003/0163287 | A1 | 8/2003 | Vock et al. |
| 2004/0006424 | A1 | 1/2004 | Joyce et al. |
| 2004/0178955 | A1 | 9/2004 | Menache et al. |
| 2005/0093698 | A1 | 5/2005 | Sakamoto et al. |
| 2005/0143199 | A1* | 6/2005 | Saroyan ............ A63B 71/0605 473/438 |
| 2005/0207617 | A1 | 9/2005 | Sarnoff |
| 2006/0087427 | A1 | 4/2006 | Le |
| 2006/0152303 | A1 | 7/2006 | Liang et al. |
| 2006/0160488 | A1 | 7/2006 | Sueoka et al. |
| 2006/0255935 | A1* | 11/2006 | Scalisi ............... B60R 25/00 340/539.13 |
| 2007/0115125 | A1* | 5/2007 | Lyon ................ G06K 7/0008 340/572.1 |
| 2007/0126558 | A1 | 6/2007 | Donato |
| 2007/0135243 | A1* | 6/2007 | LaRue .............. A63B 24/0021 473/467 |
| 2007/0182567 | A1 | 8/2007 | Stewart et al. |
| 2007/0247321 | A1 | 10/2007 | Okamoto et al. |
| 2007/0268138 | A1 | 11/2007 | Chung et al. |
| 2007/0279494 | A1 | 12/2007 | Aman et al. |
| 2007/0282482 | A1 | 12/2007 | Beucher et al. |
| 2008/0140233 | A1 | 6/2008 | Seacat |
| 2009/0048039 | A1 | 2/2009 | Holthouse et al. |
| 2009/0048044 | A1* | 2/2009 | Oleson .............. A63B 24/0062 473/570 |
| 2009/0079580 | A1 | 3/2009 | Kaplan et al. |
| 2009/0084862 | A1* | 4/2009 | McCallum .............. E01B 7/00 238/12 |
| 2009/0085724 | A1* | 4/2009 | Naressi ................ G06F 21/10 340/10.6 |
| 2009/0231198 | A1 | 9/2009 | Walsh et al. |
| 2010/0026809 | A1 | 2/2010 | Curry |
| 2010/0184563 | A1 | 7/2010 | Molyneus et al. |
| 2010/0283630 | A1 | 11/2010 | Alonso |
| 2011/0054782 | A1 | 3/2011 | Kaahui |
| 2011/0084806 | A1 | 4/2011 | Perkins |
| 2011/0205022 | A1 | 8/2011 | Cavallaro et al. |
| 2012/0065483 | A1 | 3/2012 | Chung |
| 2012/0112904 | A1 | 5/2012 | Nagy |
| 2013/0066448 | A1 | 3/2013 | Alonso |
| 2013/0096704 | A1 | 4/2013 | Case, Jr. |

OTHER PUBLICATIONS

Fraunhofer IIS 2010 Annual Report at 83 (available at http://www.eas.iis.fraunhofer.de/content/dam/eas/de/documents/iahresbericht/JB10_engl_low_res_tcm182-91049.pdf.

InMotio—Tactical, Training and Performance Management video (available at https://www.youtube.com/watch?v=dq1n7IYePJI).

International Search Report and Written Opinion issued in related PCT Patent Application PCT/US11/61718, dated Feb. 22, 2012, 12 pages.

IsoLynx Real-Time Player Tracking & Game Analysis Technology (2010), available at http://web.archive.org/web/20100604012151/http://www.finishlynx.com/isolynx/.

*Lynx System Developers, Inc. et al v. Zebra Enterprise Solutions Corporation et al.*; case No. 1:2015cv12297; United States District Court District of Massachusetts [case citation for consideration by Examiner; no NPL document provided].

Response to Written Opinion filed in related PCT Patent Application PCT/US11/61718, dated Apr. 20, 2012, 14 pages.

Zebra Intros Next-Gen RTLS Leveraging Ultra-Wideband Technology, RFID Journal available at http://www.rfidjournal.com/articles/view?7889.

Canadian Patent Application No. 2,817,998, Notice of Allowance dated Nov. 21, 2011.

European Patent Application No. 11841275.8, Official Action dated Oct. 11, 2016.

Australian Patent Application No. 2015203080, Notice of Acceptance dated Aug. 24, 2016.

(56) References Cited

OTHER PUBLICATIONS

New Zealand Application No. 704221, Notice of Acceptance dated Aug. 1, 2016.
International Preliminary Report on Patentability issued in related PCT Patent Application PCT/US11/61718, dated Nov. 15, 2012, 19 pages.
Examiner's Report for CA 2,949,476 dated Dec. 15, 2017, 3 pp.
Australian Patent Application No. 2016273813, Examination Report No. 1 dated Feb. 9, 2018 (3 pages).
Australian Patent Application No. 2016273813, Examination report dated Apr. 19, 2018, 3 pages.

\* cited by examiner

| OOI ID | DESCRIPTION | TAG ID | LOCATION |
|---|---|---|---|
| 402(1) | QUARTERBACK | PT-01 | A |
| 402(2) | HALF-BACK | PT-02 | B |
| 402(3) | LEFT TACKLE | PT-03 | C |
| 402(4) | CENTER | PT-04 | D |
| 402(5) | RIGHT TACKLE | PT-05 | E |
| 402(6) | BALL | VT-01 | A |
| 402(7) | DEFENDER 1 | PT-06 | F |
| 402(8) | DEFENDER 2 | PT-07 | G |
| 402(9) | DEFENDER 3 | PT-08 | H |

*FIG. 6A*

| VIRTUAL TAG | ACTUAL TAG | ASSOCIATED TAG |
|---|---|---|
| VT-01 | BT-01 | PT-01 |

*FIG. 6B*

ASSOCIATIVE OBJECT TRACKING SYSTEMS AND METHODS

RELATED APPLICATIONS

This application is a continuation of U.S. patent application Ser. No. 15/163,242, filed May 24, 2016, which is a continuation of U.S. patent application Ser. No. 13/301,614, filed Nov. 21, 2011, now U.S. Pat. No. 9,375,628 which issued Jun. 28, 2016, which claims the benefit of priority to U.S. Patent Application No. 61/415,707, titled "Associative Object Tracking Systems and Methods", filed Nov. 19, 2010, each of which is incorporated herein by reference in its entirety.

BACKGROUND

When tracking tags are attached to objects to be tracked, such as players of a sport for example, the identity of the tracking tag must be associated with the player. This is typically a manual process where a person manually identifies (e.g., reads the serial number off the tag) and manually enters that number into a database in association with the identity of the object to which it is attached. This process is particularly error-prone where tag numbers are typically sequential, as are the player identification numbers. Where tracking tag allocation occurs before a game, there is a possibility of the player collecting an incorrect tracking tag, or accidentally swapping the tracking tag with that of another player, just prior to the game. In each case, incorrect identification information entered into the database results in incorrect tracking information. Further, where a tracking tag fails, the allocation of a new tracking tag requires that the database be amended with the identity of the new tracking tag that replaces the failed one; this again is a potential problem where conditions (e.g., at the sideline of a sports field) are not ideal for successful data entry.

When tracking objects that are moving unpredictably, the tracking system often loses 'contact' with the tracked object, such as when a player in a sporting event moves behind another player. Systems that visually track objects require an uninterrupted line of sight from the tracking device (e.g., camera) to the object being tracked. When the object is not imaged, tracking is not possible. Similarly, with a wireless tracking system that uses radio waves to locate an object being tracked, if the radio signal is blocked then tracking of that object is not possible. When tracking (visual or radio) is blocked temporarily, the lost information results in poor quality of the tracking information.

Achieving uninterrupted tracking of certain objects of interest "OOI" in a sporting event, such as a football or a hockey puck, presents unique challenges as these objects frequently lack line of site "LOS" to detection devices (receivers, cameras, etc.) positioned around the field of play. With tag based systems, continuous tracking can become sporadic in the absence of LOS. With optically based systems, continuous tracking is impossible in the absence of LOS.

SUMMARY

In one embodiment, a method tracks a first object when continuous tracking information for the first object is not available. The method detects when the tracking information for the first object is not available and, if tracking information for the first object is not available, performs the steps of: determining a last time of a last determined location of the first object, determining a second object closest to the last determined location at the last time, and associating the location of the first object with a location of the second object.

In another embodiment, an associative tracking apparatus tracks a first object using tracking information for the first object and tracking information for a second object. A tracking reliability monitor determines when the tracking information for the first object is not reliable. A proximity detector identifies the second object as closest to the first object when the tracking reliability monitor determines that the tracking information for the first object is not reliable. An associative tracker associates a location of the first object with a location of the second object when the tracking reliability monitor determines that the tracking information for the first object is not reliable.

In another embodiment, a method tracks a first object using tracking information for a second object. Proximity of the first object to the second object is sensed. An indication of the sensed proximity is transmitted with the tracking information for the second object. A tracking apparatus receiving the tracking information detects when tracking information for the first object is not available and the location of the first object is associated with a location determined from the tracking information when the tracking information for the first object is not available.

In another embodiment, a system tracks a first object using tracking information for a second object. The system includes a generator for generating a proximity signal relative to the first object. A sensor configured with the second object detects the proximity signal and a transmitter, configured with the second object, transmits tracking information for the second object and an indication of proximity of the first object to the second object based upon detection of the proximity signal.

In another embodiment, a method automatically associates a tracking tag with a tracked object. An object identity (ID) of the object located within a detection area is determined. A tracking ID of the tracking tag is determined from a radio signal received from the tracking tag and is associated, within a database, with the object ID.

In another embodiment, a system automatically assigns a tracking tag to an object to be tracked. The system includes a receiver for receiving a wireless signal from the tracking tag and an assignment device for determining a tracking tag identity (ID) of the tracking tag based upon the wireless signal, for determining an object ID of the object when positioned within a detection area, and for associating the tracking tag ID with the object ID within a database.

BRIEF DESCRIPTION OF THE FIGURES

FIG. 6A shows one exemplary table storing information of OOI and assigned tracking tags, in an embodiment.

FIG. 6B shows one exemplary virtual tag table that associates virtual tag IDs with the actual tracking tags assigned to OOI, in an embodiment.

DETAILED DESCRIPTION OF THE DRAWINGS

Figure 1A:
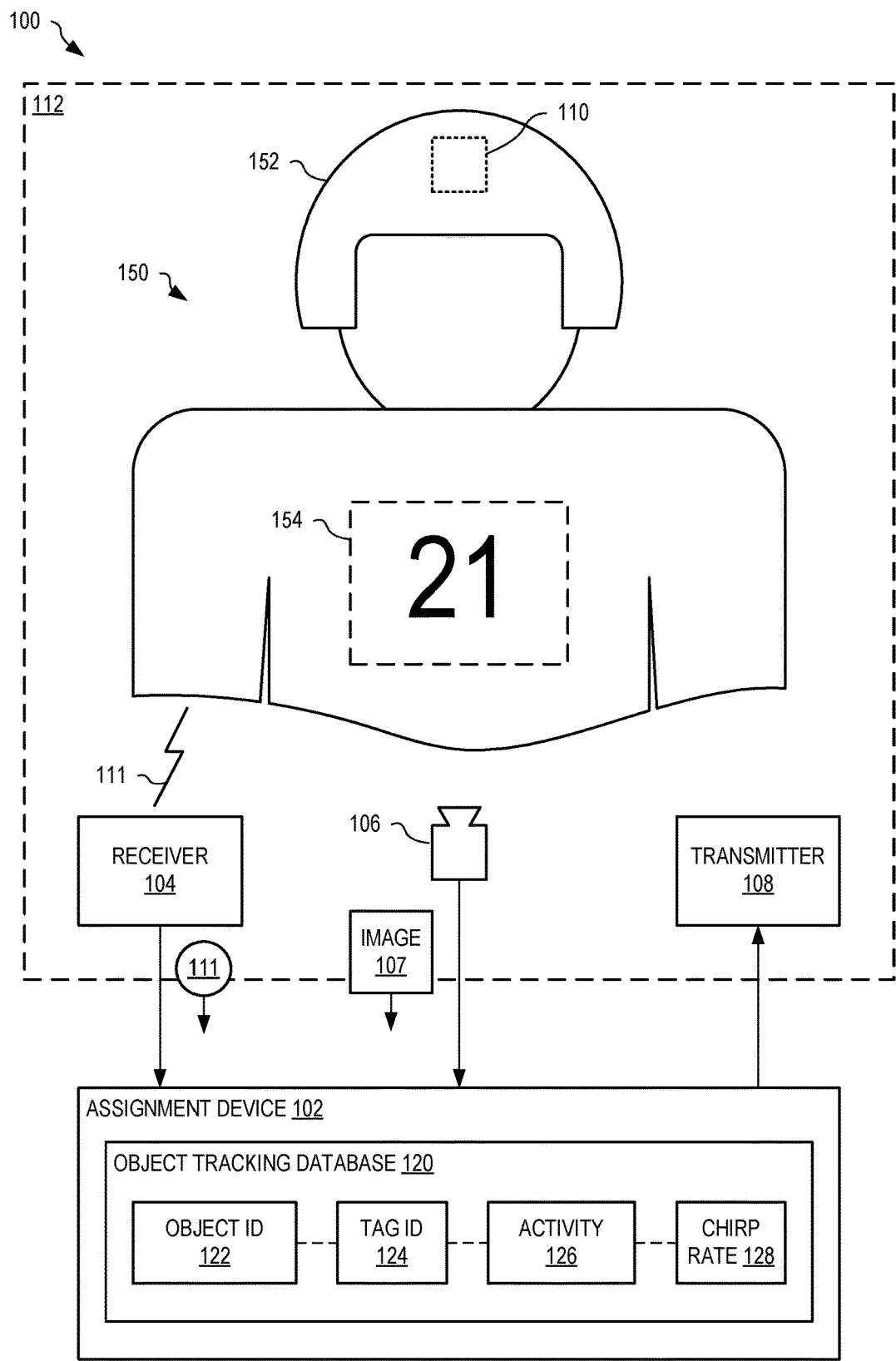
FIG. 1A shows one exemplary tracking tag assignment system that identifies an object to be tracked using a camera, in an embodiment.

FIG. 1A shows one exemplary tracking tag assignment system 100. System 100 includes an assignment device 102, a receiver 104, a camera 106, and a transmitter 108. Receiver 104, camera 106, and transmitter 108 operate within a detection area 112. Objects to be tracked have one or more tracking tags 110 attached therewith. Typically, each object that is tracked also has visually identifying features, such as one or more of a competitor number, an identification number, and biometric features. In the example of FIG. 1, a football player 150 wearing a jersey with an identification number 154 and a helmet 152 that includes a tracking tag 110 enters detection area 112 and is imaged by camera 106. Although football is used as an example in FIG. 1, system 100 may perform tracking tag assignment to other objects, such as athletes for other sports, vehicles, and so on.

Figure 1B:
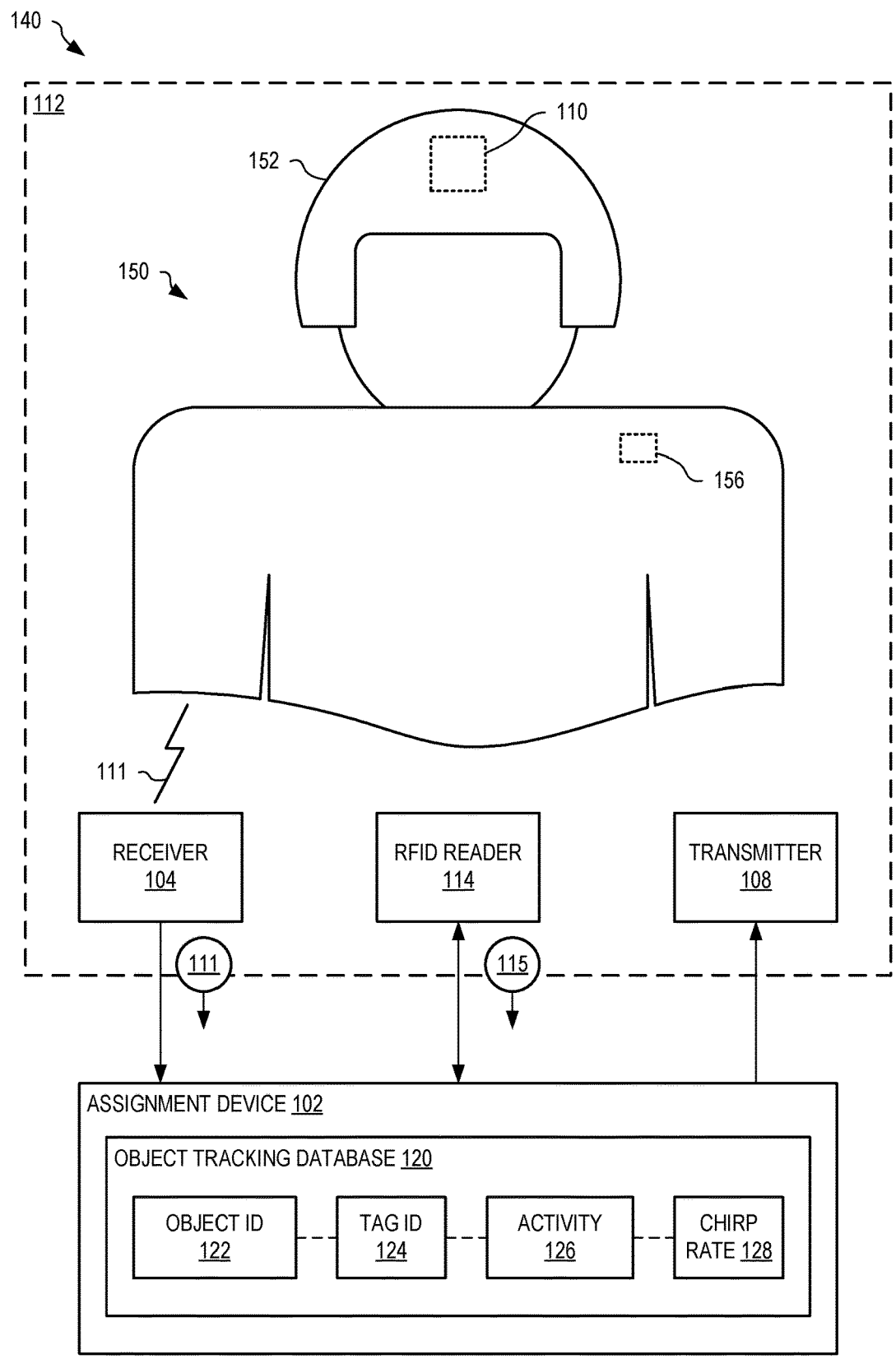
FIG. 1B shows one exemplary tracking tag assignment system that reads an RFID tag attached to the object being tracked, in an embodiment.

FIG. 1B shows a tracking tag assignment system 140 configured with an RFID reader 114 for reading an RFID tag attached to the object being tracked by tracking tag 110. In place of camera 106, as included within system 100, system 140 includes RFID reader 114. Under control of assignment device 102, RFID reader 114 reads information including an RFID tag ID from an RFID tag 156 that is attached to player 150. For example, RFID tag 156 may be built into equipment worn by player 150, such as the player's jersey, wherein information within the RFID tag may indicate the player's number printed on the jersey. Information read from RFID tag 156 thereby allows assignment device 102 to identity the player. Other information may be included within the RFID tag, such as a team number, without departing from the scope hereof. In the embodiment of system 140, detection area 112 represents an operational area of RFID reader 114, such as defined by the wireless range of RFID reader 114.

It should be noted that tracking tag 110 provides at least location information in real time and is considered an 'active' tag. RFID tag 156, on the other hand, is a passive tag that stores information and can be read using an RFID reader.

Similarly, a football may be manufactured to include an RFID tag 156 and a tracking tag 110. Information stored in the RFID tag indicates that the object is a football, thereby allowing assignment device 102 to assign the tracking tag ID of the included tracking tag to an identification number (e.g., the RFID tag ID) of the football. Assignment device 102 may assign tracking tags to many footballs that are used within a game, and although these footballs may be indistinguishable from each other, a tracking system (e.g., tracking system 400, FIG. 4) may use the assignment information to identify the football used for each game play.

Where assignment device 102, receiver 104, RFID reader 114, and transmitter 108 are combined into a portable unit together with wireless networking capability, this portable unit, through cooperation with a tracking system (e.g., tracking system 400) over the wireless network, may provide portable tracking tag assignment, thereby facilitating replacement of failed tracking tags during a game. For example, by including a tracking tag with the portable unit, the tracking system may correlate the location of the portable unit with the location of the tracking tag identified by assignment device 102.

Figure 2:
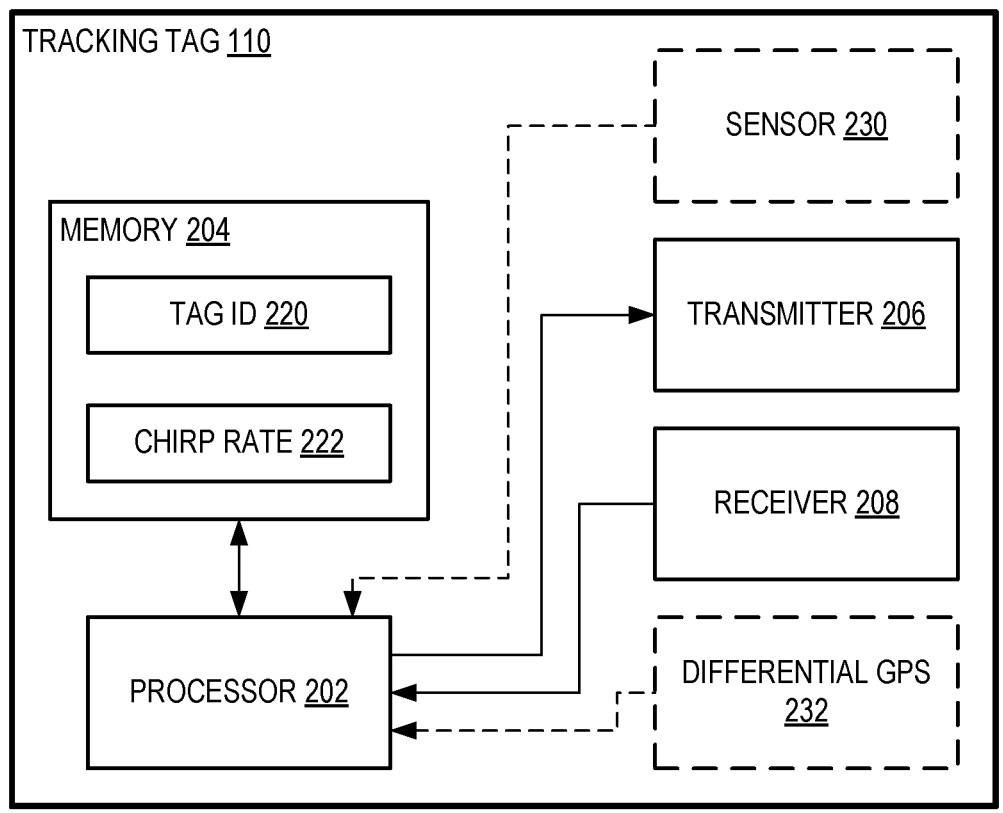
FIG. 2 shows the tracking tag of FIG. 1 in further exemplary detail.

FIG. 2 shows tracking tag 110 of FIGS. 1A and 1B in further exemplary detail. Tracking tag 110 includes a processor 202, a memory 204, a transmitter 206, and a receiver 208. Optionally, tracking tag 110 includes one or more sensors 230 and/or a differential GPS locator 232. FIGS. 1A, 1B, and 2 are best viewed together with the following description.

In one embodiment, transmitter 206 of tracking tag 110 and receiver 104 utilize ultra-wideband (UWB) for radio location of tracking tag 110. Other means of locating tracking tag 110 may be used without departing from the scope hereof.

When player 150 is within detection area 112, camera 106 captures at least one image 107 of identification number 154 on player 150, and receiver 104 receives a signal (chirp) 111 from tracking tag 110. Detection area 112 may be conveniently located such that each player 150 passes through detection area 112 to enter the playing field, for example Assignment device 102 receives signal 111 from tracking tag 110, via receiver 104, and receives image 107 from camera 106. Assignment device 102 uses known techniques to identify player 150 within image 107 and includes an object tracking database 120 that has a list of players (e.g., player 150) and their associated identification information. Database 120 may include other information, such as the player's position on the team (e.g., quarterback, running back, center, lineman, etc.).

In the example of FIG. 1A, identification number 154 is captured within image 107 taken by camera 106, and the identification number "21" of player 150 is determined by assignment device 102, for example by using optical character recognition, as known in the art. Assignment device 102 then performs a look-up of the player's number ("21") within database 120 and assigns, to the identified player 150, the tracking tag ID (e.g., tag ID 220, FIG. 2) received within signal 111 from tracking tag 110. Assignment device 102 automatically assigns a tag ID 124 of tracking tag 110 to the identity (e.g., an object ID 122) of player 150 within database 120. For example, tag ID 220 is stored in database 120 as tag ID 124. The use of system 100 eliminates human error in assigning tag IDs with objects being tracked.

In the example of FIG. 1B, information is read from RFID tag 156 by RFID reader 114 and the identity of player 150 is determined. For example, information read from RFID tag 156 may include the jersey identification number "21" of player 150. RFID tag 156 information is communicated to assignment device 102 as a message 115. Assignment device 102 then performs a look-up of the player's number ("21") within database 120 and assigns the tracking tag ID (e.g., tag ID 220, FIG. 2) received within signal 111 from tracking tag 110 to the identified player 150. Assignment device 102 automatically assigns tracking tag ID 220 of tracking tag 110 (e.g., as tag ID 124) to the identity (e.g., object ID 122) of player 150 within database 120. The use of system 140 eliminates human error in assigning tracking tag IDs with objects being tracked.

Database 120 may also contain information relating to an expected activity 126 of each tracked object (e.g., player 150). Using the football example of FIG. 1, activity 126 may represent the field position of the player, and thus his expected movement on the field during play. Based upon this expected activity and/or field position, defined within activity 126, a chirp rate 128 may be defined for tracking tag 110. Characteristics of tracking tag 110 may be preset to a default configuration.

Upon associating object ID 122 with tag ID 124 of tracking tag 110, assignment device 102 utilizes transmitter 108 to set a chirp rate 222 of tracking tag 110. Transmitter 108 operates to communicate wirelessly with receiver 208 of tracking tag 110 based upon one or more of radio waves, magnetic induction coupling, and infrared. Assignment device 102 may set other parameters of tracking tag 110.

Tracking tag 110 may automatically enter a low power mode to save energy (and to increase battery life for example). For example, tracking tag 110 may enter a low power mode after a defined period, such as the duration of a game plus one hour. Assignment device 102 activates tracking tag 110 by wirelessly setting characteristics of tracking tag 110. For example, in low power mode, tracking tag 110 may reduce its chirp rate to save power, wherein assignment device 102 sets the chirp rate 222 characteristic of tracking tag 110 based upon expected activity of the object being tracked. In low power mode, tracking tag 110 may also shut down any included sensors 230 to conserve power, wherein assignment device 102 sets characteristics of tracking tag 110 to configure sensor 230 operation. For example, assignment device 102 may configure sensors 230 by setting characteristics including one or more of sensor configuration (e.g., which sensor is active), sensor resolution (e.g., bits per reading), update rate (how often it sends data), threshold settings (e.g., where the sensor only reports when the sensed value is above or below specified thresholds), and a mode of sensor operation (e.g., average, maximum, and minimum values).

In one example of operation, tracking tag 110 includes sensors 230 to sense certain biometrics of player 150, such as heart rate, oxygen level, respiration rate, and so on. Assignment device 102 uses transmitter 108 to set characteristics of sensors 230 to sample certain biometric characteristics of player 150 based upon known physiological traits of the player. Where use of certain sensors 230 within tracking tag 110 is not needed, these sensors may be configured by assignment device 102 to remain inactive to save power.

Continuing with the football example of FIG. 1, if system 100 determines, based upon database 120 information, that player 150 plays as a wide receiver, system 100 utilizes transmitter 108 to set the chirp rate of tracking tag 110 to a high rate/frequency to improve tracking accuracy, since the wide receiver is expected to run quickly and change direction unpredictably. On the other hand, if system 100 determines, based upon database 120 information, that player 150 plays as a lineman, system 100 uses transmitter 108 to set the chirp rate of tracking tag 110 to a lower frequency, since less movement is expected of the lineman.

System 100, 140 automatically identifies an object (e.g., player 150) within detection area 112, determines an ID of one or more tracking tags 110 attached to that object, and assigns the identified tracking tags to the identified object. Further, system 100, 140 may also configure characteristics of the identified tracking tags 110 based upon the expected activities of the identified object. Thereby, system 100, 140 avoids potential human error in populating object tracking database 120 when tracking tags are assigned to players prior to a game.

Should tracking tag 110 become inoperable, a new tracking tag 110 may be attached to the object (e.g., player 150) and automatically assigned to the object by system 100, 140 when the player is within detection area 112.

Figure 3A:
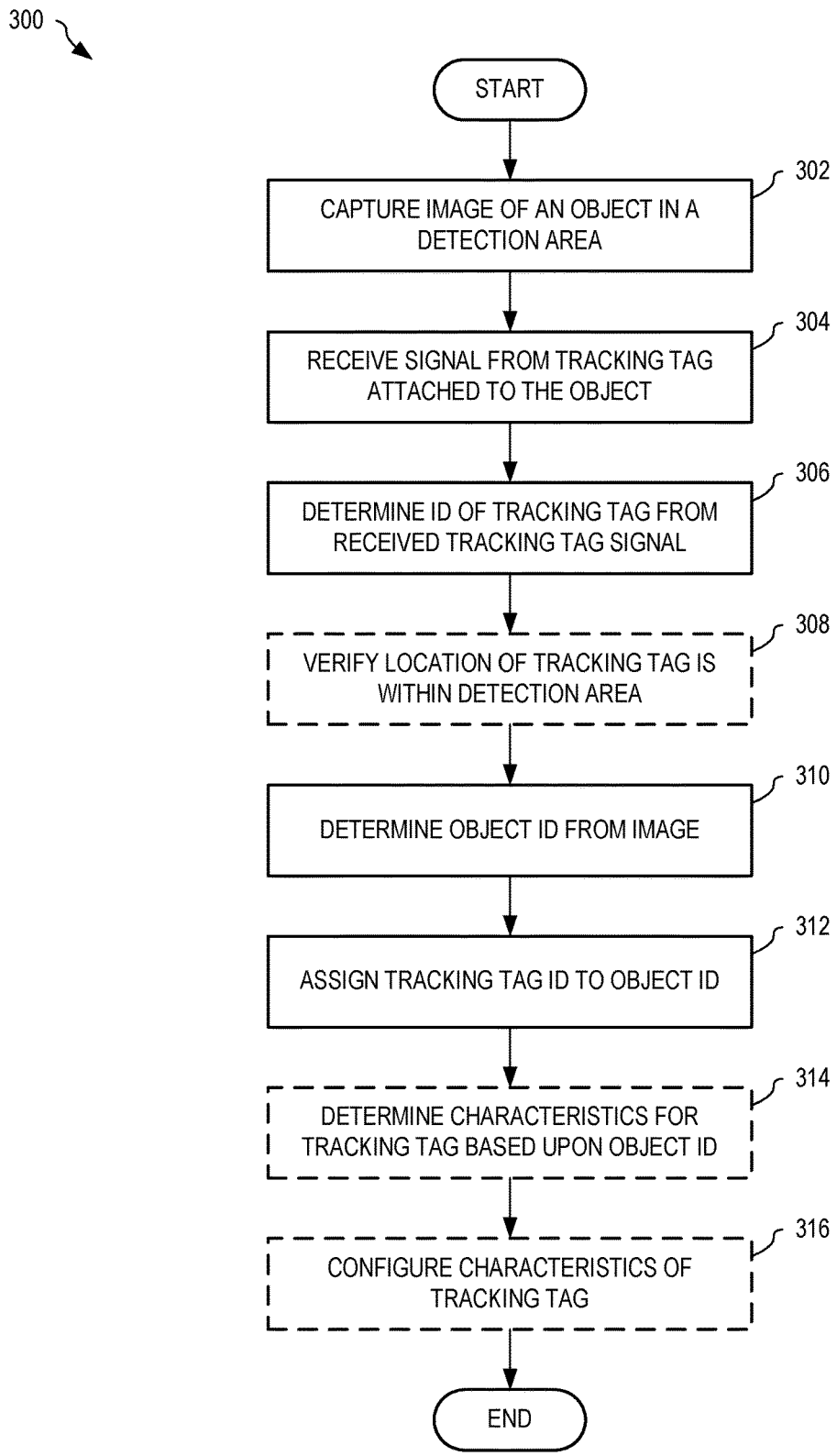
FIG. 3A is a flowchart showing one exemplary method for assigning a tracking tag ID to a tracked object identified by a camera, in an embodiment.

FIG. 3A shows one exemplary method 300 for assigning a tracking tag ID to a tracked object (e.g., player 150). Method 300 is for example implemented within assignment device 102 of FIG. 1. In step 302, method 300 utilizes a camera to capture an image of an object in a detection area. In one example of step 302, assignment device 102 controls camera 106 to capture image 107 of player 150 within detection area 112. In step 304, method 300 utilizes a receiver to receive a signal from the tracking tag attached to the object. In one example of step 304, assignment device 102 receives a signal 111 from tracking tag 110 via receiver 104. In step 306, method 300 determines, e.g., within assignment device 102, the ID of the tracking tag from the received tracking tag signal. In one example of step 306, assignment device 102 determines tag ID 220 from signal 111.

Step 308 is optional. In step 308, if included, method 300 verifies, within assignment device 102, that the location of the tracking tag is within the detection area. In one example of step 306, if implemented, assignment device 102 receives a determined location of the tracking tag from a tracking apparatus (e.g., tracking apparatus 408, FIG. 4), and verifies that the identified tracking tag is located within detection area 112. Optional step 308 provides additional security for determining that the identified tracking tag is attached to the object within detection area 112.

In step 310, method 300 determines, within assignment device 102, an object ID from the image captured in step 302. In one example of step 310, assignment device 102 identifies player 150 based upon optical character recognition of identification number 154 on the jersey of player 150 within image 107. In step 312, method 300 assigns, within assignment device 102, the determined tracking tag ID to the determined object ID. In one example of step 312, assignment device 102 stores determined tracking tag ID 220 as tag ID 124 within object tracking database 120, and in association with determined object ID 122.

Steps 314 and 316 are optional. In step 314, if included, method 300 determines, within assignment device 102, characteristics for the tracking tag based upon the determined object ID. In one example of step 314, assignment device 102 determines a chirp rate 128 associated with activity 126 of object ID 122 from database 120. In step 316, if included, method 300 configures, controlling transmitter 108 from assignment device 102, characteristics of the tracking tag. In one example of step 316, assignment device 102, using transmitter 108, sets chirp rate 222 of tracking tag 110 based upon chirp rate 128 determined in step 314.

Steps of method 300 may occur in a different order without departing from the scope here; for example, step 301 may occur after step 306 or step 308.

Figure 3B:
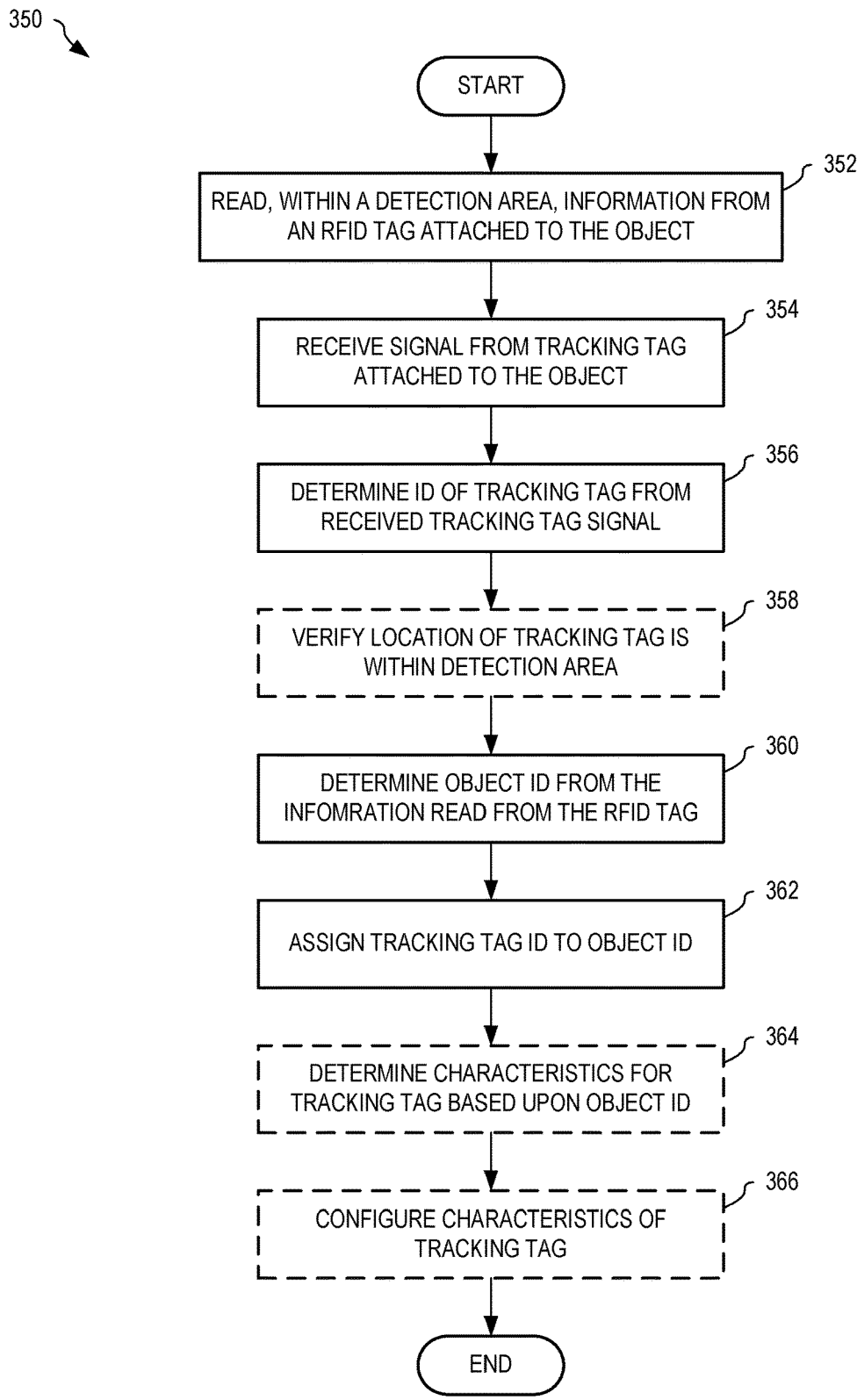
FIG. 3B is a flowchart showing one exemplary method for assigning a tracking tag ID to a tracked object identified by an RFID tag, in an embodiment.

FIG. 3B shows one exemplary method 350 for assigning a tracking tag ID (e.g., tag ID 220) to a tracked object (e.g., player 150) using an RFID reader (e.g., RFID reader 114). Method 350 is for example implemented within assignment device 102 of FIG. 1B. In step 352, method 350 reads, using an RFID reader controlled by assignment device 102, information from an RFID tag that is attached to the tracked object within a detection area. In one example of step 352, assignment device 102 controls RFID reader 114 to read, within detection area 112, information from RFID tag 156 that is attached to a jersey of player 150. The information for example contains at least an RFID tag ID and a jersey number. In step 354, method 350 receives, within assignment device 102, a signal from the tracking tag attached to the object. In one example of step 354, assignment device 102 receives a signal 111 from tracking tag 110 via receiver 104. In step 356, method 350 determines, within assignment device 102, the ID of the tracking tag from the received tracking tag signal. In one example of step 356, assignment device 102 determines tag ID 220 from signal 111.

Step 358 is optional. In step 358, if included, method 350 verifies, within assignment device 102, that the location of the tracking tag is within the detection area. In one example of step 358, if implemented, assignment device 102 receives a determined location of tracking tag 110 from a tracking apparatus (e.g., tracking apparatus 408, FIG. 4), and verifies that the identified tracking tag is located within detection area 112. Optional step 358 provides additional security for determining that the identified tracking tag is attached to the object within detection area 112.

In step 360, method 350 determines, within assignment device 102, the object ID from the information read from the RFID tag in step 352. In one example of step 360, assignment device 102 identifies player 150 based upon the jersey number stored within the information read from RFID tag 156 and transmitted as message 115. In step 362, method 350 assigns, within assignment device 102, the determined tracking tag ID to the determined object ID. In one example of step 362, assignment device 102 stores determined tracking tag ID 330 as tag ID 124 within object tracking database 120 and in association with determined object ID 122.

Steps 364 and 366 are optional. In step 364, if included, method 350 determines, within assignment device 102, characteristics for the tracking tag based upon the determined object ID. In one example of step 364, assignment device 102 determines a chirp rate 128 associated with activity 126 of object ID 122 from database 120. In step 366, if included, method 350 configures, using transmitter 108 controlled by assignment device 102, characteristics of the tracking tag. In one example of step 366, assignment device 102, using transmitter 108, sets chirp rate 222 of tracking tag 110 based upon chirp rate 128 determined in step 364.

Steps of method 350 may occur in a different order without departing from the scope here; for example, step 352 may occur after step 356 or 358.

Figure 4:
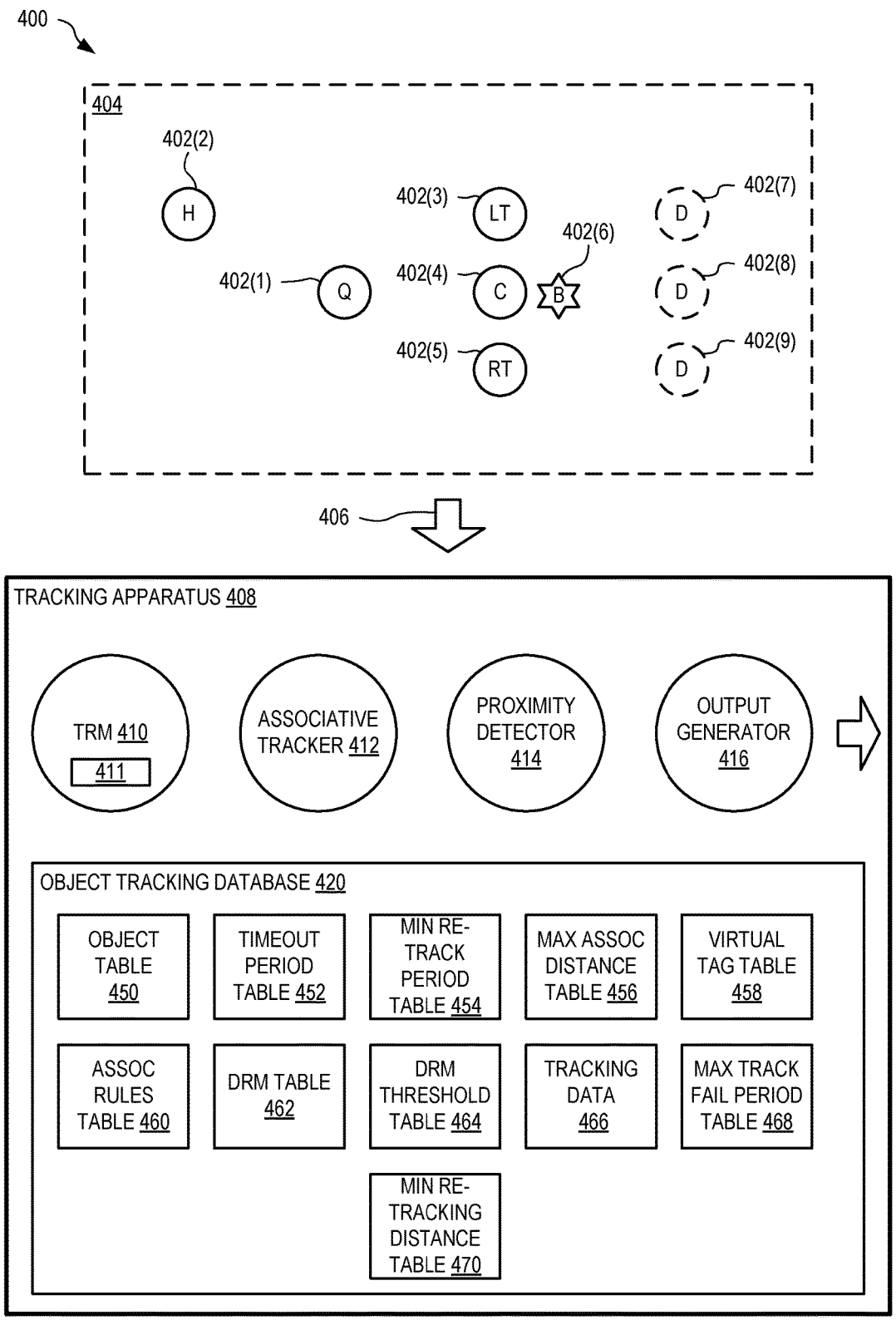
FIG. 4 shows one exemplary associative object tracking system tracking objects of interest (OOI) during a football game within an operational area, in an embodiment.

FIG. 4 shows one exemplary associative object tracking system 400 tracking objects of interest (OOI) 402 during a football game within an area 404. Area 404 represents the playing field for the football game, for example and OOI 402 includes players 402(1-5) and 402(7-9), officials, and game equipment, such as a football 402(6) for a football game and a puck for a hockey game. In particular, OOI 402(1)-402(5) are football players (e.g., player 150, FIG. 1) of a first team, OOI 402(6) is a football, and OOI 402(7)-402(9) are football players of a second team.

A tracking apparatus 408 receives tracking information 406 and tracks each OOI 402 within area 404. Tracking apparatus 408 has an object tracking database 420 that is used to store tracking information of OOI 402. Database 420 may be implemented within memory of a computer system (e.g., a server) for example In one embodiment, database 420 is a relational database that stores operational parameters, tracking data and other information of system 400. Database 420 is illustratively shown with an object table 450, a timeout period table 452, a minimum re-track period table 454, and a maximum association distance table 456. Object table 450 stores OOI identification information and assignment of tracking devices. Timeout period table 452 stores a timeout period for each tracking tag and/or OOI 402. Minimum re-track period table 454 stores a re-track period for each tracking tag and/or OOI 402. Maximum association distance table 456 stores a maximum distance for which an association may occur for each tracking tag and/or OOI 402. A virtual tag table 458 stores a list of virtual tags that may be assigned to one or more OOI 402 (e.g., ball OOI 402(6)) and an associated tag that is used to determine a location of the virtual tag during associative tracking. Database 420 may also include an associative rules table 460 that defines additional (i.e., in addition to those defined within tables 452, 454, 456 and 458) rules for associative tracking and is described in detail further below.

In one embodiment, each OOI 402 has at least one tracking tag (e.g., tracking tag 110) that send signals to receivers (not shown) of tracking apparatus 408. Tracking apparatus 408 may include functionality of system 100, 140 that automatically assigns tracking tags to each OOI. In another embodiment, tracking apparatus 408 has two or more cameras (not shown) that track each OOI 402 visually within area 404. Tracking apparatus 408 may operate with any type of object tracking method.

Tracking apparatus 408 periodically, for example, determines and/or receives tracking information 406 for each OOI 402 within area 404 and determines and stores location information for each OOI 402 based upon tracking information 406. However, when tracking information from an OOI 402 is temporarily blocked, such as when line of sight from that OOI to the detecting device (e.g., camera and/or radio receiver) is blocked by another object, location data for that OOI cannot be directly determined.

In the example of FIG. 4, OOI 402(6) represent a football that is often hidden from view and has its line-of-sight path to the detecting device (e.g., camera and/or radio receiver) blocked by other OOI, such as when the football is shielded from view during a play. Since location of OOI 402(6) is occasionally missed, tracking apparatus 408 is configured to associate the blocked OOI with a nearest tracked OOI based upon proximity when the data was first missed. The following continues with the football example of FIG. 4; however, tracking apparatus 408 and associative tracking may be used in other applications. For example, system 400 and associative tracking may also be used in basketball and soccer.

Figure 5A:
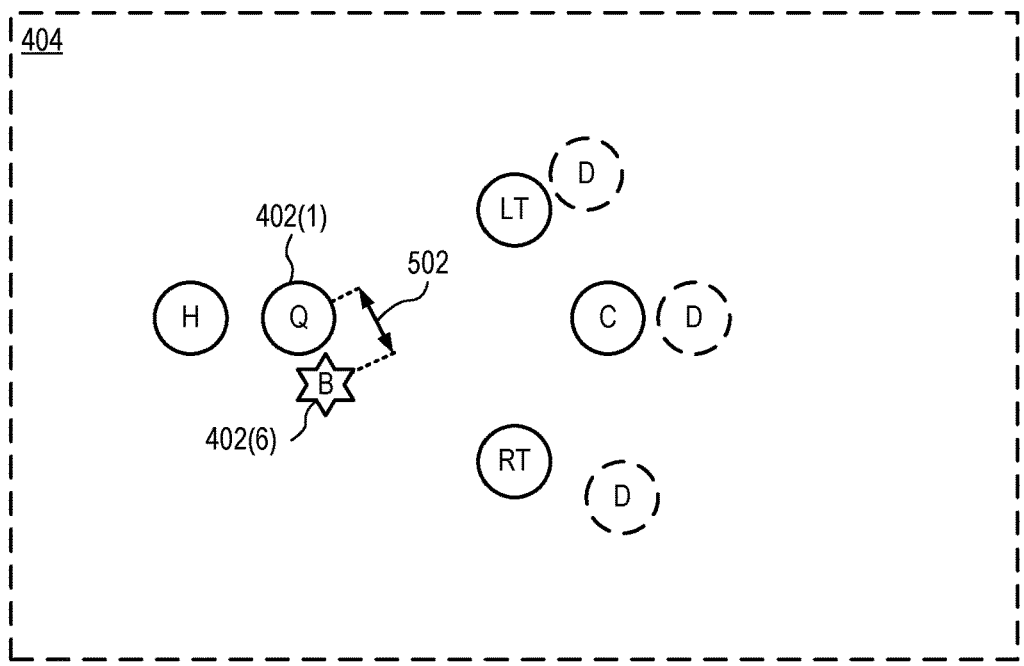
FIG. 5A is a snapshot diagram showing exemplary positions of the OOIs, as determined by the tracking apparatus of FIG. 4, a short period after the positions illustrated in FIG. 4.
Figure 5B:
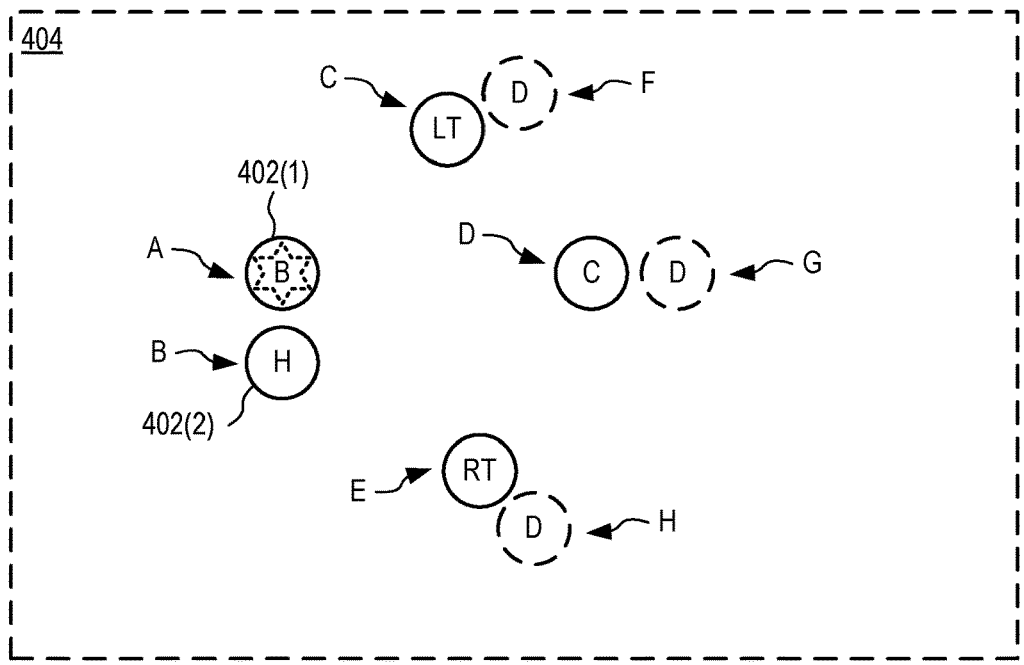
FIG. 5B is a snapshot diagram showing positions of the OOIs, as determined by the tracking apparatus of FIG. 4, a short time after the snapshot of FIG. 5A.

FIG. 5A is a snapshot showing exemplary positions of OOI 402 in area 404 as determined by tracking apparatus 408 a short period after the positions illustrated in FIG. 4. Specifically, in the football example shown, the snap has occurred and a Quarterback 402(1) has or is receiving ball 402(6). Quarterback 402(1) and ball 402(6) are separated by a distance 502. FIG. 5B is a snapshot showing positions of the players, as determined by tracking apparatus 408, a short time after the snapshot of FIG. 5A. However, the tracking signal of ball 402(6) is blocked by Quarterback 402(1) and thus the location of the ball cannot be directly determined by tracking apparatus 408 from tracking information 406.

Tracking apparatus 408 utilizes a tracking reliability monitor (TRM) 410 to determine a data reliability metric (DRM) 411 for tracking information 406 received for each tracked object 402. DRM 411 is a relative measurement of how reliable each determined location is. Within database 420, a DRM table 462 may store the latest DRM 411 for each tracked object 402. Database 420 also includes a DRM threshold table 464 that defines a DRM threshold for each tracked object 402. This DRM threshold defines a minimum DRM value For example, associative tracker 412 may use DRM 411 and an associated DRM threshold from DRM threshold table 464 to determine when tracking information 406 for OOI 402(6) is not reliable enough for use, or is missing. TRM 410 may include a timer that determines when tracking information 406 for each tracked object 402 is not received and thereby reduce the DRM 411 for that tracked object. For example, where tracking information 406 is expected from OOI 402(6) every 300 ms, TRM 410 may reduce the associated DRM 411 for each 310ms period that tracking information 406 for OOI 402(6) is not received. Where DRM 411 is below its associated DRM threshold, TRM 410 triggers an associative tracker 412 that associates OOI 402(6) with a closest tracked object. In one embodiment, DRM 411 is determined for tracking information received for each tracked OOI 402.

TRM 410 determines DRM 411 for each determined location of each OOI 402. Where location of OOI 402 is derived from multiple detectors positioned around the operational area 404 (e.g., radio receivers in the case of tracking tags and cameras in the case of visual tracking), location may be determined in more than one way, for example using different combinations of detector. Ideally, each location determined from each of the different combinations of detectors would result in substantially the same determined location. However, in reality, each detector combination typically generates a slightly different location for the OOI 402. In one embodiment, DRM 411 is derived from a measurement of the spread between the locations determined for a particular OOI 402 from each different detector combination. The greater the spread in these determined locations, the lower the DRM 411 for that determined location. In the football example of FIG. 4, where DRM 411 is below a DRM threshold defined within DRM threshold table 464 for ball 402(6), associative tracker 412 is triggered to associate ball 402(6) with the nearest other player 402.

With visual tracking systems using more than three cameras (not shown), DRM is similarly calculated. With the visual tracking system, DRM may also be based upon a calculated reliability of the image recognition (e.g., of recognizing the ball within the captured images).

Once triggered, associative tracker 412 determines a last location and time determined from received tracking information 406 for the blocked OOI 402(6) and then determines the closest other OOI 402 at that time. For example, if football 402(6) was last determined as proximate to Quarterback 402(1), as shown in FIG. 5A, Quarterback 402(1) would be automatically identified as the closest other OOI 402. Associative tracker 412 then associates the location of football 402(6) with that of Quarterback 402(1), until further location information 406 from football 402(6) is again received by tracking apparatus 408. That is, the location of football 402(6) is updated as the location of Quarterback 402(1) changes. When location information 406 of football 402(6) is again received by tracking apparatus 408, the location of football 402(6) is determined from the received location information.

Figure 8A:
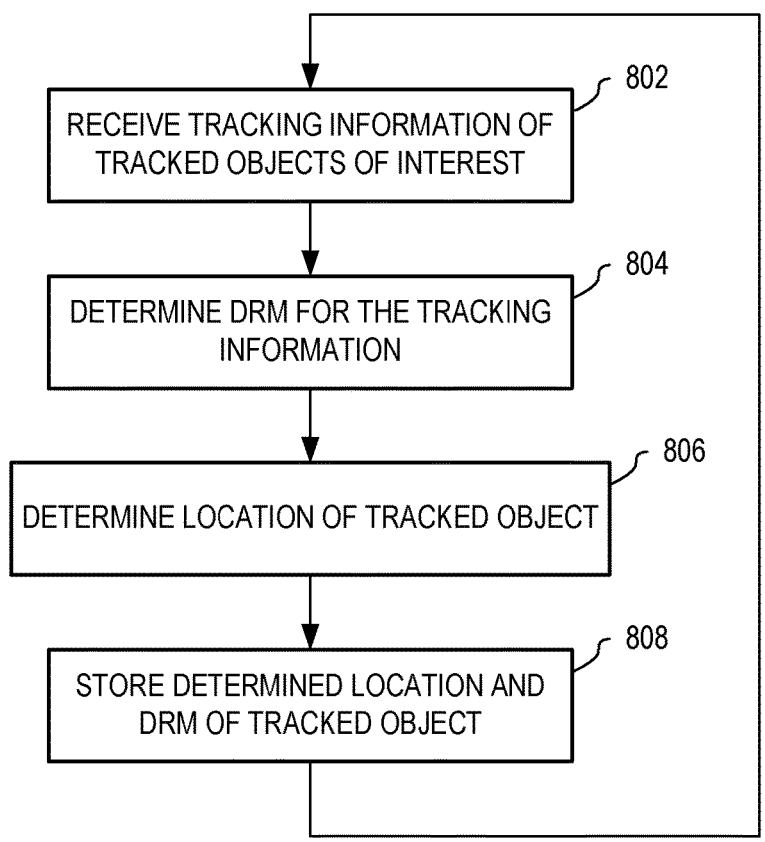
FIGS. 8A and 8B are flowcharts illustrating exemplary methods for processing received tracking information and associatively tracking OOIs when tracking information is not received, in an embodiment.
Figure 8B:
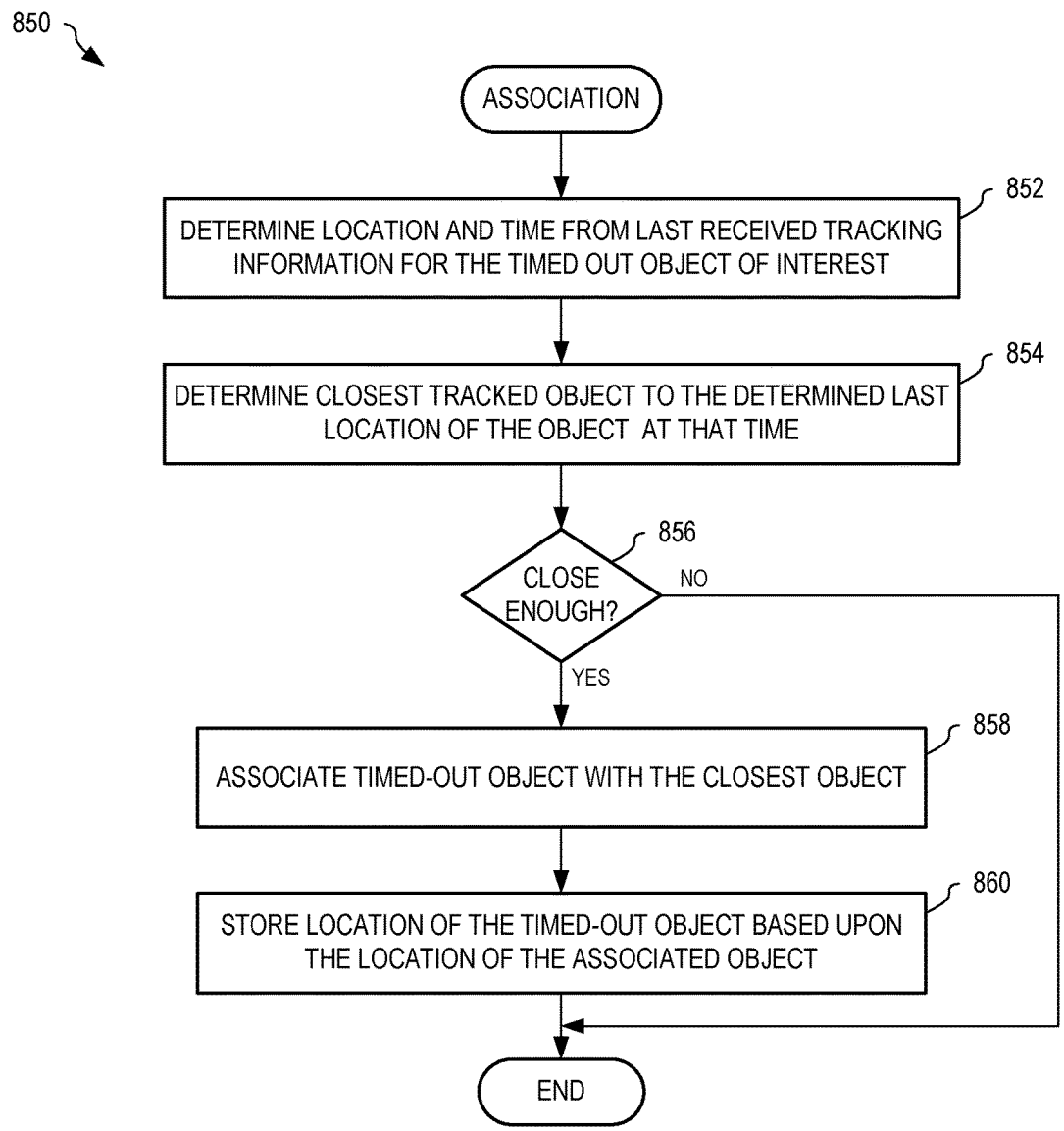

FIGS. 8A and 8B are flowcharts illustrating exemplary methods for processing received tracking information within tracking apparatus 408 and associative tracking for when tracking information is not received. Respective methods 800 and 850 are for example implemented within tracking apparatus 408, FIG. 4. In step 802, method 800 receives tracking information of tracked objects of interest. In one example of step 802, tracking apparatus 408 receives tracking information 406 of OOI 402. In step 804, method 800 determines DRM 411 for the tracking information of the tracked object. In one example of step 804, TRM 410 determines DRM 411 from tracking information 406 for OOI 402(6). In step 806, method 800 determines a location of the tracked object based upon the tracking information. In one example of step 806, tracking information 406 is decoded to determine the location of OOI 402(6). In step 808, method 800 stores the determined location and DRM of the tracked object. In one example of step 808, tracking apparatus 408 stores the determined location of OOI 402(6) within tracking data 466 of database 420 and store the determined DRM 411 within database 420. Steps 802 through 804 repeat for received tracking information.

Method 850 is invoked when DRM 411, determined in step 804 of method 800, falls below a DRM threshold, which indicates that the tracking information cannot be used to locate the associated OOI 402. Method 850 is invoked for each OOI 402 for which tracking information is not received or cannot be used. In step 852, method 850 determines the last location and last time for received tracking information for the timed-out OOI. In one example of step 852, where method 850 is invoked for OOI 402(6), associative tracker 412 determines, from tracking data 466, a last determined location and time for OOI 402(6), shown in the snapshot of FIG. 5A. In step 854, method 850 determines a closest tracked object to the determined last location and at the determined last time. In one example of step 854, associative tracker 412 invokes a proximity detector 414 to identify Quarterback 402(1) as being the closest OOI 402 to ball 402(6) at the determined last time, as shown in the snapshot of FIG. 5A.

Step 856 is a decision. If, in step 856, method 850 determines that the closest OOI identified in step 854 is close enough for associative tracking, method 850 continues with step 858; otherwise, method 850 terminates. In step 858, method 850 associates the timed-out object with the closest object. In one example of step 858, associative tracker 412 stores the ID of a tracking tag PT-01 within a virtual tag VT-01 of ball 402(6), within table 650 (FIG. 6B, described below), to associate ball 402(6) with Quarterback 402(1). In step 860, method 850 stores the location of the timed-out object based upon the location of the associated object. In one example of step 860, associative tracker 412 stores a location 'A' of Quarterback 402(1) within row 612 and column 608 of table 600 (FIG. 6A, described below) as the associative location of ball 402(6).

Smooth Associative Tracking

Although the above associative tracking improves the tracking of OOI that temporarily become hidden from view and/or have tracking information blocked, certain erratic behavior may result since occasional loss of tracking data does occur. Intermittent association and disassociation of an object with another object because of very temporarily missed location information may be perceived as 'jumping' or 'flickering' of the tracked position as the object switches position between an associated location and a derived location. As noted above, it is normal that tracking information is occasionally lost or blocked. For example, a signal from a tracking tag may be temporarily blocked by another object. Similarly, an object may be temporarily blocked by other objects from view by a visual tracking system.

To prevent such flickering, system 400 utilizes configurable parameters that control when associative tracker 412 associates and disassociates a first OOI with a second tracked OOI. For example, by comparing DRM 411 to a DRM threshold (or two thresholds such as association and disassociation DRM thresholds), and using a maximum tracking fail period and minimum re-tracking period, erratic associative jumping and flickering is minimized Tracking apparatus 408 may include DRM threshold table 464 that specifies the DRM threshold (optionally a DRM threshold for association and a DRM threshold for disassociation), a maximum track fail period table 468 that specifies, for each OOI 402, the maximum track fail period, and minimum re-track period table 454 that specifies, for each OOI 402, the minimum re-track period. In one example of operation, if DRM 411 of tracking information falls below the DRM threshold (or is missing) for at least the maximum track fail period, associative tracker 412 is triggered to associate location of OOI 402 with another OOI. Similarly, if location for an OOI is associated with another OOI, TRM 410 triggers associative tracker 412 when tracking information 406 from that OOI is above the DRM threshold stored within DRM threshold table 464 for more than the minimum re-track period stored within minimum re-track period table 454.

Further, tracking apparatus 408 may also include a minimum re-tracking distance table 470 that specifies a minimum re-tracking distance. When tracking information is again received for the OOI, if the distance between the location derived from the tracking information and the location of the OOI to which the association is made is greater than the minimum re-tracking distance, the OOI may be disassociated. The use of minimum re-track period table 454 and minimum re-tracking distance table 470 prevents erratic tracking of the object where tracking information 406 is intermittent.

Tracking apparatus 408 may also have a maximum association distance 456 that defines a maximum distance over which a tracking association may be formed. For example, associative tracker 412 may associate football 402(6) with Quarterback 402(1) when distance 502 between the two is less than the maximum association distance stored within maximum association distance table 456. The maximum association distance is for example 2 feet within a football game. However, where used to track players in other sports, the maximum association distance may be specified for that sport. In lacrosse, for example, the maximum association distance may be 4 feet. In one embodiment, minimum re-track period table 454, maximum association distance table 456, maximum track fail period table 468, minimum re-tracking distance table 470, DRM threshold table 464, and associative rules table 460 are configured based upon the sport being tracked.

In one embodiment, each OOI 402 is assigned a tracking tag (e.g., automatically assigned by system 100, 140, FIGs. 1A, 1B). This physical assignment of tracking tags is recorded within database 420.

FIG. 6A shows one exemplary table 600 storing information of OOI and assigned tracking tags. An OOI ID column 602 stores an identity of each OOI being tracked by system 400. For clarity of this example, the identification number of OOIs within FIG. 4A are shown within column 602; however, other identification may be used without departing from the scope hereof. For example, a player's jersey number may be used for identification within column 602. A description column 604 is shown for clarity of illustration and is optional. Column 604 provides a description of the OOI being tracked, and in this example indicates the position of the player on the football field, or the ball. A tag ID column 606 stores the ID of the tracking tag assigned to the OOI being tracked. In one embodiment, column 606 is populated automatically by system 100, FIG. 1. In an alternate embodiment, column 606 is manually populated. A location column 608 stores the determined location of the OOI being tracked. Location column 608 is updated by tracking apparatus 408 as tracking information 406 is received. For example, location A is determined from tracking information 406 received from tracking tag PT-01 that assigned to Quarterback 402(1), as indicated in row 610 of table 600. Location A is therefore inserted into location column 608 of row 610 as the current location of OOI 402(1).

Information of OOI 402(6) is stored in row 612 of table 600, which indicates that OOI 402(6) is a ball (column 604) that is assigned a virtual tag ID "VT-01" in column 606. Although OOI 402(6) does have tracking tag BT-01 assigned to it (see FIG. 6B), the use of virtual tag ID "VT-01" within table 600 facilitates associative tracking of the ball by system 400.

FIG. 6B shows one exemplary virtual tag table 650 which, within row 660, associates virtual tag ID "VT-01" in column 652 with the actual tracking tag "BT-01" in column 654 that is assigned to OOI 402(6). An associated tag column 656 allows the virtual tag identified in column 652 to be associated with another tracking tag, illustratively shown as tracking tag ID "PT-01." Associated tag column 656 is populated when tracking data from actual tag BT-01 is not received and associative tracker 412 utilized proximity detector 414 to determine a nearest tracking tag for association with virtual tag "VT-01".

Although only OOI 402(6) (the ball in the example of FIG. 4) is shown with assigned virtual tag, other tracked OOI may also be assigned virtual tags where associative tracking is desired.

Enhanced Associative Tracking

In real world scenarios, where players intentionally hide the ball in an attempt to deceive opponents, tracking systems that do not employ association, human camera operators, and spectators alike are likely also deceived. Even when an associative tracking methodology is used, there will be instances where additional intelligence must be built into the system in order to ensure the highest level of continuous and accurate OOI tracking. Particularly where a change of ball possession occurs while the ball is hidden.

To improve associative tracking, additional intelligence may be incorporated into associative tracker 412 to enhance tracking of OOIs when tracking information is unreliable or is missing. This additional intelligence may be based upon specific sport knowledge, wherein the probability of certain scenarios is predetermined and used by tracking apparatus 408 together with a probability threshold for associative transfers. By using this additional intelligence, tracking apparatus 408 will increase the likelihood of making correct associations.

Figure 7A:
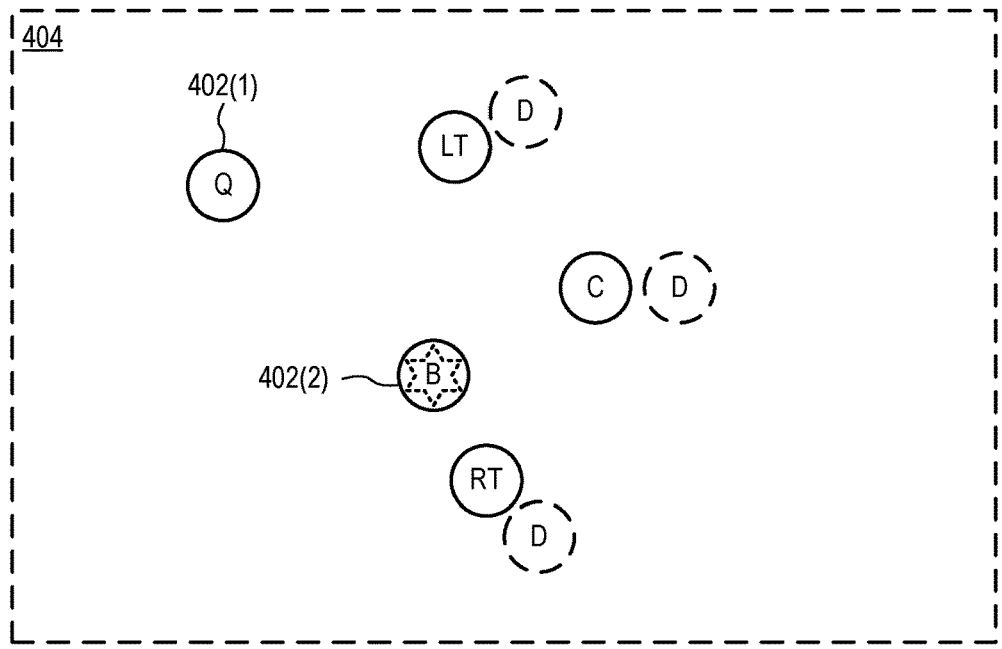
FIGS. 7A and 7B show two exemplary snapshots of later positions of players within the area.
Figure 7B:
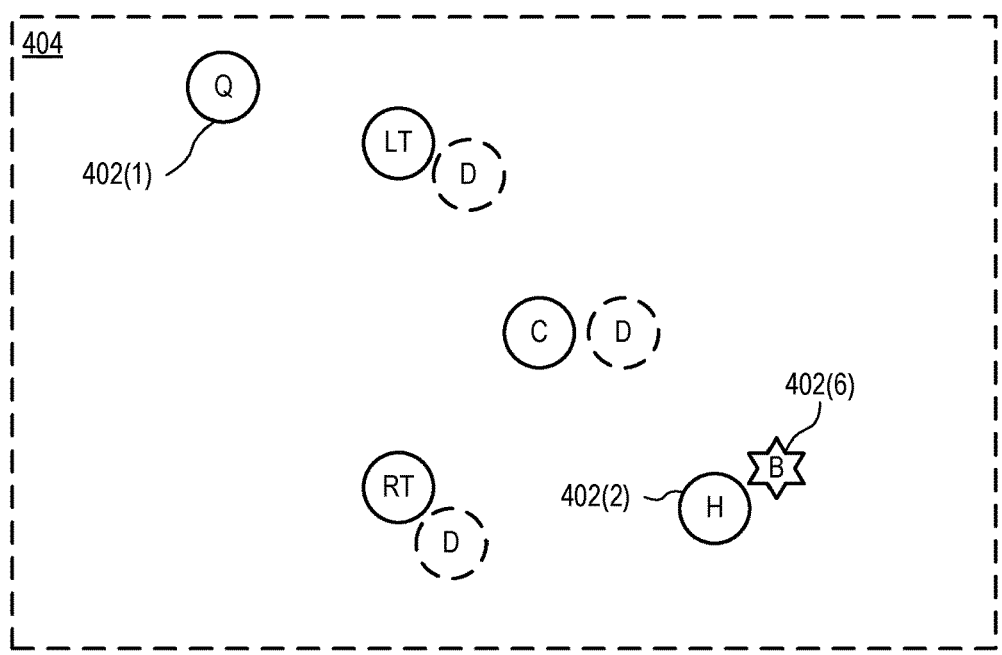

FIGS. 7A and 7B show two later snapshots of positions of players within area 404. FIGS. 5A, 5B, 7A, and 7B thus show a sequence of events in chronological order and are best viewed together with the following description.

As noted above and shown in FIG. 5A, Quarterback 402(1) was closest to ball 402(6) when tracking information 406 of ball 402(6) was blocked, and thus the location of ball 402(6) is associated with Quarterback 402(1), and shown collocated with Quarterback 402(1) in FIG. 5B. As known to those that follow football, it is likely that Quarterback 402(1) is intentionally hiding ball 402(6) in an attempt to deceive the opposing team. While tracking information of ball 402(6) is not available, additional intelligence may be used by associative tracker 412 to track movements of ball 402(6) based upon movements of other OOI 402.

In a first example of applying additional intelligence to associative tracking, the snapshot of FIG. 5B shows that Quarterback 402(1) and Half-back 402(2) have come into contact with (or at least very close to) one another, and in this example, Quarterback 402(1) hands ball 402(6) to Half-back 402(2), who also keeps ball 402(6) covered to further deceive the opposing team. Additional intelligence within tracking apparatus 408 indicates that a ball transfer between a Quarterback and a Half-back is likely, and therefore ball 402(6) becomes associated with Half-back 402(2) and disassociated with Quarterback 402(1).

Specifically, tracking apparatus 408 includes associative rules table 460 within object tracking database 420 to define when close proximity of a player with an associative ball is likely to transfer the ball to the other player. For example, associative rules table 460 may define a probability of transfer between each player on a team.

In FIG. 7A, Quarterback 402(1) has continued to stay 'in the pocket', while Half-back 402(2) has advanced with the ball, although tracking information 406 of ball 402(6) is still not received by tracking apparatus 408. In FIG. 7B, Half-back 402(2) has continued to run forwards with ball 402(6), and tracking information 406 of ball 402(6) is again received by tracking apparatus 408 and the location of ball 402(6) is derived directly (i.e., without association).

Continuing with the exemplary scenario of FIG. 7A, as described above, associative tracker 412 has associated ball 402(6) with the location of Half-back 402(2), since Half-back 402(2) came into contact with Quarterback 402(1) while ball 402(6) was associated with Quarterback 402(1). Specifically, intelligence within tracking apparatus 408 has determined that ball 402(6) is most probably carried by Half-back 402(2). However, if an associative transfer of ball 402(6) has been made and tracking information 406 for ball 402(6) is momentarily received, but not received for long enough that ball would be disassociated with Half-back 402(2), associative tracker 412 may re-evaluate the associative transfer of the ball 402(6). For example, associative tracker 412 may re-evaluate the transfer of association of ball 402(6) from Quarterback 402(1) to Half-back 402(2). If associative tracker 412 determines that the momentary tracking information indicates that the transfer is incorrect (e.g., that the location of ball 402(6) is closer to Quarterback 402(1) that to Half-back 402(2)), associative tracker 412 may reverse the earlier associative decision and associate ball 402(6) with Quarterback 402(1). Provided the momentary tracking information 406 is of sufficient reliability (e.g., using DRM 411) to resolve the proximity of ball 402(6) to players involved in an associative transfer, associative tracker 412 may correct associative transfers that prove incorrect.

Further, where output of tracking apparatus 408 is provided to a delayed feed, associative transfer decisions may be resolved prior to output, such that the user (e.g., a viewer) of the tracking information from an output generator 416 receives higher quality tracking information. Effectively, using the look-ahead allowed by a delayed feed, speculative associative transfers may be resolved prior to output of the location information from output generator 416. See FIG. 12 and the associated description below.

In another example, where ball 402(6) is associated with Quarterback 402(1), and Quarterback 402(1) comes into contact with Left Tackle 402(3), additional intelligence within tracking apparatus 408 determines that a ball transfer between Quarterback 402(1) and Left-Tackle 402(3) is not likely, and therefore ball 402(6) remains associated with Quarterback 402(1) in this example.

Due to the unpredictable nature of sports, even with additional intelligence, there will be instances where tracking information of the OOI is not available and a likely transfer between players does not happened or an unlikely transfer does happen. In these instances, regardless of whether or not the correct association is made, the position of the OOI is immediately resolved once the tracking information is again received.

Association Assignment by Proximity Sensing

In the vast majority of situations, system 400 makes a correct association between a first OOI (e.g., ball 402(6)) and a second OOI (e.g., Quarterback 402(1)). However, since system 400 is not receiving tracking information from the first OOI, the possibility exists that an incorrect association is made and is not detected until the tracking information for the associated OOI is again received (e.g., when the DRM 411 of ball 402(6) rises above the DRM threshold).

To improve reliability of associative tracking, local proximity sensing is used to associate a first OOI with a second OOI, which eliminates incorrect association of the first OOI (e.g., ball 402(6)) with a tracked OOI (e.g., Half-back 402(2)) when a probable association is incorrect.

Figure 9:
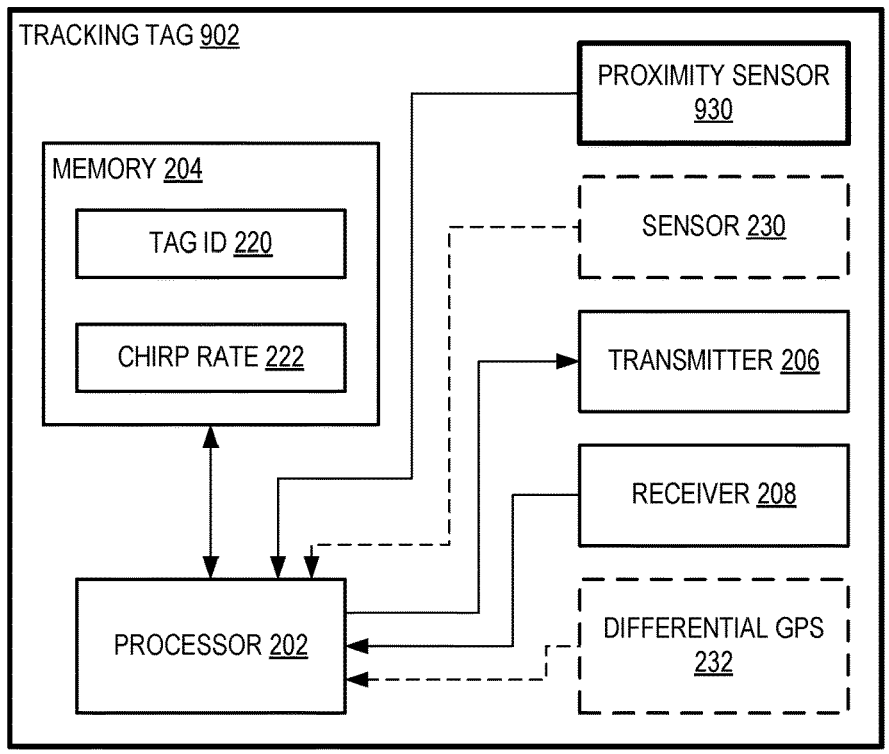
FIG. 9 shows one exemplary tracking tag, similar to the tracking tag of FIG. 2, which also includes a proximity sensor.
Figure 10:
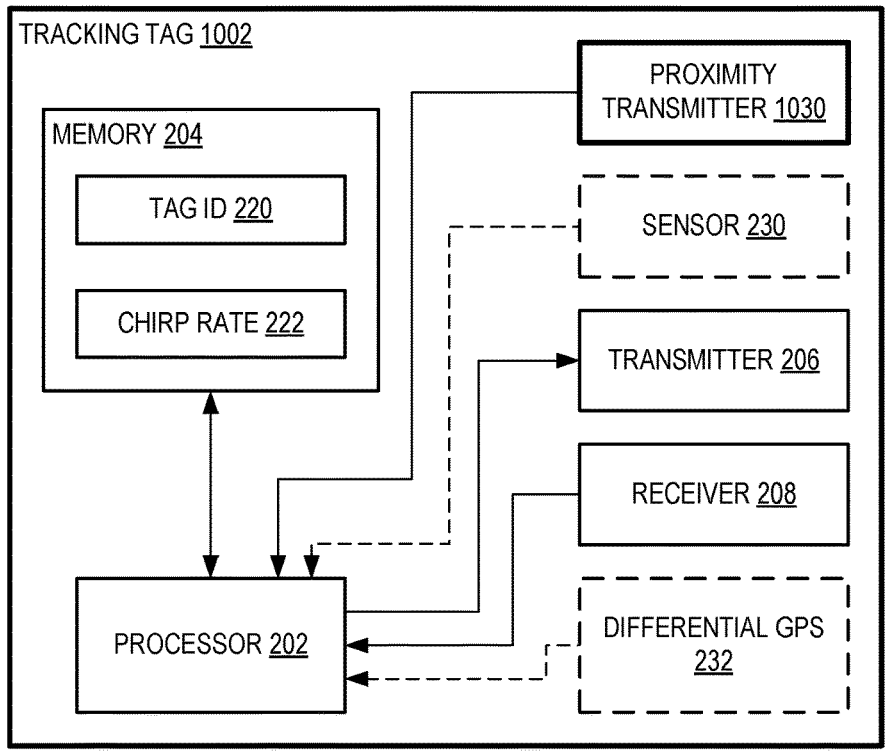
FIG. 10 shows one exemplary tracking tag, similar to the tracking tag of FIG. 2, which also includes a proximity transmitter.

FIG. 9 shows one exemplary tracking tag 902, similar to tracking tag 110 of FIG. 2, which also includes a proximity sensor 930. FIG. 10 shows one exemplary tracking tag 1002, similar to tracking tag 110 of FIG. 2, which also includes a proximity transmitter 1030. FIGS. 9 and 10 are best viewed together with the following description. Proximity transmitter 1030 generates a proximity signal that has a limited range. Proximity sensor 930 detects the signal (i.e., an electromagnetic signal) from proximity transmitter 1030 provided that proximity sensor 930 is within the limited range of proximity transmitter 1030. In one example, proximity transmitter 1030 has a range of two feet, wherein the maximum distance between tracking tag 1002 and tracking tag 902 where proximity sensor 930 is able to detect the proximity signal from proximity transmitter 1030 is two feet. The proximity signal is for example one of a short range wireless signal and a magnetic signal. In one embodiment, proximity transmitter 1030 is a magnet and proximity sensor 930 is a magnetic detector. The range of proximity transmitter 1030 is for example selected based upon a sport being tracked. The above example of two feet is based upon using tracking tag 1002 within football, whereas a range of four feet (or more) may be selected for tracking tag 1002 where it is incorporated within a lacrosse ball.

Proximity transmitter 1030 continuously emits the proximity signal such that tracking tag 902 may detect when tracking tag 1002 is within range (e.g., within two feet). In one example of operation, tracking tag 902 is attached to a football player (e.g., Quarterback 402(1)) and tracking tag 1002 is fabricated within a football (e.g., ball 402(6)). When, within tracking tag 902, proximity sensor 930 detects the proximity signal from proximity transmitter 1030, processor 202 determines that tracking tag 1002 is within range of tracking tag 902 and sets an "OOI Proximity" bit within a tracking signal (e.g., a chirp) transmitted by transmitter 206 of tracking tag 902. This OOI proximity bit is cleared by processor 202 when proximity sensor 930 indicates that the proximity signal is not detected. In an alternate embodiment, where tracking information is determined visually through use of two or more cameras, transmitter 206 of tracking tag 902 transmits a wireless signal containing the OOI proximity bit and identification information of the transmitter such that a receiver of the signal may determine that the first OOI is proximate to the second, particularly when the visual tracking information is blocked.

It should be noted that proximity detection of tracking tag 1002 by tracking tag 902 occurs within tracking tag 902 and does not require location information to be derived for either tracking tag 902 or tracking tag 1002 to determine their proximity to one another. Specifically, tracking tag 902 may determine when tracking tag 1002 is proximate thereto (within range) independently of other tracking functionality.

Where tracking tags 902 and 1002 are used within system 400, for example in place of tracking tags 110, OOI proximity information is transmitted by transmitter 206 as part of the "chirp" used to locate tracking tag 902. The OOI proximity information received within tracking information 406 is used by associative tracker 412, in conjunction with location information derived from tracking information 406, to associate one object with another when location information for that object cannot be determined. For example, when DRM 411 of ball 402(6) falls below the DRM threshold defined within DRM threshold table 464, associative tracker 412 determines which tracking tag, or tracking tags, have their OOI proximity bit set, and associates tracking ball 402(6) accordingly. If more than one tracking tag 902 indicates OOI proximity, then these tracking tags, and associated OOI (e.g., players) are close together such that association may be made to any one of them. Where multiple tracking tags 902 indicate OOI proximity, association may be based upon additional rules, such as: sport specific knowledge that defines a probability ranking of the tracked objects (e.g., players) for association, and association history wherein, if the associative probability of the objects indicating OOI proximity is equal, the association is made with the one object having the most recent previous association.

The advantage of determining association of one object to another based upon OOI proximity information, as compared to determining association based upon the last known position of the OOI, is realized when the tracked objects separate and the number of tracking tags 902 indicating OOI proximity is reduced to one. The remaining OOI proximity indication allows the association to the correct objects to approach 100% reliability, even when the location information for the associated object cannot be determined.

Where location of an object cannot be determined and association to a second object is based upon one or more of last known location, historical data and sport specific knowledge, a high probability of correct association may be achieved. Where that association is also based upon proximity detection, the probability of correct association increases to 100%, particularly as the indication of OOI proximity reduces to a single OOI.

Figure 11:
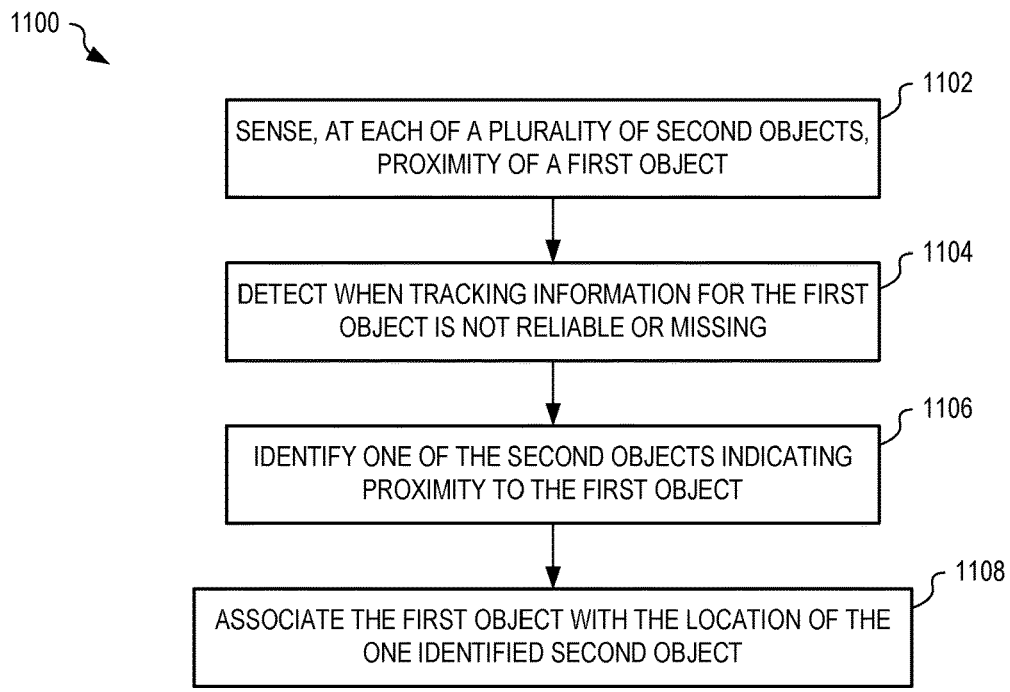
FIG. 11 is a flowchart illustrating one exemplary method for tracking a first object for which sufficient continuous tracking information is not available.

FIG. 11 is a flowchart illustrating one exemplary method 1100 for tracking a first object for which sufficient continuous tracking information is not available. Method 1100 is for example implemented within tracking apparatus 408, FIG. 4. In step 1102, method 1100 senses, at each of a plurality of second objects, proximity of the first object. In one example of step 1102, tracking tag 1002, FIG. 10, is attached to a football (first object) and a tracking tag 902, FIG. 1, is attached to each of a plurality of football players (second objects), wherein each tracking tag 902 senses when tracking tag 1002 is proximate using proximity sensor 930 to detect a proximity signal from proximity transmitter 1030. In step 1104, method 1100 detects when tracking information for the first object is not reliable or missing. In one example of step 1104, tracking apparatus 408 determines that tracking information for the ball (first object) is blocked based upon DRM 411 of tracking tag 1002. In step 1106, method 1100 identifies one of the second objects indicating proximity to the first object. In one example of step 1106, tracking apparatus 408 receives an indication of proximity to tracking tag 1002 from one tracking tag 902 of one player (second object). In step 1108, method 1100 associates the first object with the location of the one identified second object. In one example of step 1108, associative tracker 412 of tracking apparatus 408 associates the ball (first object) with the one identified player (second object) of step 1106.

Delayed Feed for Associative Transfer Resolution

The methods of object association described above are based upon identifying a single point in time when the location of a first object cannot be determined (or where reliability is below a defined threshold), and determining the most likely second object with which to associate the first object. Until location information for the first object can be determined again (or until reliability returns above a defined threshold), tracking the first object is based upon one or more rules defined for the sport being tracked. In a simple example, the first object remains associated with the second object until location information for the first object is determined again. However, even when enhanced associative tracking (described above) is applied, incorrect association of a 'hidden' object may occur where an unexpected action occurs with the object.

Figure 12:
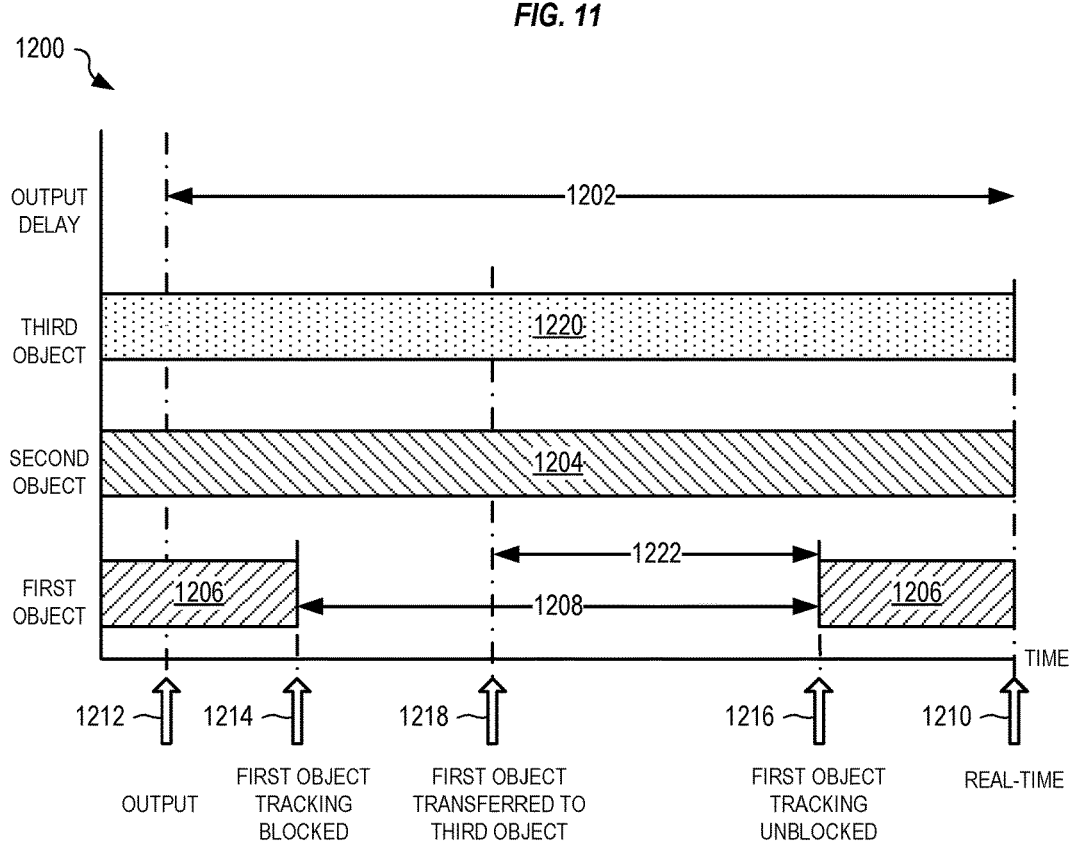
FIG. 12 is a graph illustrating exemplary timing of object tracking information in association with a feed delay period.

FIG. 12 is a graph 1200 illustrating exemplary timing of object tracking information output in association with a delay period 1202. That is, object tracking information is delayed from real-time 1210 by period 1202 prior to output from system 400. For example, output of object tracking data may be associated with a delayed video feed, as known in the art where image processing is performed on the frames of captured video prior to outputting the frames, such as occurs for the "yellow line" in football.

In the example of FIG. 12, tracking of a second object 1204 and a third object 1220 (e.g., football players) by system 400 is substantially continuous, but tracking of a first object 1206 (e.g., a football) is blocked at time 1214 for a period 1208 until tracking information of first object 1206 is unblocked at time 1216. Based upon associative tracking methods described above, at time 1214, first object 1206 is associated with second object 1204, nearest at that time. At time 1218, second object 1204 and third object 1220 come into close proximity of one another, but rule evaluation within system 400 maintains the association of first object 1206 with second object 1204. At time 1216, when tracking information of first object 1206 is no longer blocked, system 400 determines that first object 1206 is not near second object 1204, but is near third object 1220. Thus, although not determined likely by system 400, first object 1206 was transferred to third object 1220 at time 1218, and for a period 1222 first object 1206 was incorrectly associated with second object 1204. System 400 then modifies the stored associative tracking information for first object 1206 such that first object 1206 is associated with third object 1220 for period 1222. Since tracking information is delayed for period 1202, the associative tracking information is corrected by system 400 prior to output.

The use of delay period 1202 allows system 400 to verify and correct associative tracking, if necessary, prior to output of the tracking information. Specifically, by configuring delay period 1202 to be greater than an expected maximum period (e.g., period 1208) of blocked tracking information, system 400 corrects tracking associations before they are output from system 400, thereby improving accuracy of associative tracking. That is, system 400 may correct associate tracking errors that occur within delay period 1202, even if the tracking information for the associated object was blocked for a longer period.

Specifically, when location information is received for first object 1206 after period 1208, system 400 evaluates the determined location of first object 1206 against the location of associated second object 1204. If the distance between the locations of the first object and the second object is greater than a predefined threshold for associative tracking, system 400 then identifies the object closest to the first object, and then traces the possession back to time 1218 when the transfer of first object from second object to third object occurred. Within the stored data, this transfer is indicated by close proximity of second object 1204 to third object 1220 at time 1218. System 400 then modifies the stored data to indicate the associative transfer of first object 1206 to third object 1220 from second object 1204 at time 1218, thereby correcting the associative tracking information prior to its output from system 400.

From a viewer's perspective, when watching a display generated from object tracking data output by system 400 for the above example, the transfer of the ball (first object 1206) from a first player (second object 1204) to a second player (third object 1220) is indicated within the tracking data at the correct time. For example, where object tracking data is output from system 400 and accompanies a delayed video feed, the position of the ball is indicated correctly by the tracking data, even when it is not clear from the displayed video.

Where system 400 provides tracking information for "off-line" viewing, for example for viewing after a game has finished, delay period 1202 is effectively the duration of the game thereby allowing system 400 to detect and correct, if necessary, associative transfers for the entire game, prior to the object tracking data being viewed and/or used. In one example of operation, object tracking data from system 400 is processed by a computer to generate a graphical representation of players and the ball within football field. In another example of operation, object tracking data from system 400 is processed by a computer to generate a textual display that lists the number (and optionally other information) of the player that has possession of the ball during a football game.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for annotating a delayed feed of a sporting activity with tracking information determined within a tracking apparatus for a plurality of objects, comprising:
   determining when continuous location tracking information for a primary one of the plurality of objects is not available;
   when, for a period when the continuous location tracking information for the primary object is not available and based upon a highest probability defined within one or more predetermined scenarios of the sporting activity, speculatively associating the primary object with a first one of two secondary ones of the plurality of objects that are proximate a last location of the primary object;
   when the continuous location tracking information for the primary object becomes available after the period, receiving an updated location for the primary object and evaluating correctness of the speculative association of the primary object with the first secondary object based upon the updated location, to produce a non-speculative association of the primary object with one of the secondary objects; and
   outputting the delayed feed with the tracking information for the first object based upon tracking information of the non-speculatively associated one of the secondary objects during the period when the continuous location tracking information is not available.

2. The method of claim 1, the step of outputting comprising:
   when the step of evaluating determines that the speculative association is correct, outputting tracking information for the primary object to the delayed feed during the period, to define the location of the primary object as the location of the first secondary object; and
   when the step of evaluating determines that the speculative association is incorrect, outputting tracking information for the primary object to the delayed feed during the period to define the location of the primary object as the location of the other of the two secondary objects.

3. The method of claim 1, the continuous location tracking information for the primary object being determined by wirelessly receiving a signal transmitted by a tracking tag attached to the primary object.

4. The method of claim 1, in the step of speculatively associating, the first secondary object being non-speculatively associated with the primary object prior to the step of speculatively associating.

5. The method of claim 1, the step of determining when continuous location tracking information for the primary object is not available comprising determining a data reliability measurement (DRM) for the continuous location tracking information, wherein the continuous location tracking information is determined to not be available when the DRM is below a DRM threshold.

6. The method of claim 1, the step of speculatively associating comprising speculatively associating the primary object with the first secondary object according to the one or more associative rules of the predetermined scenarios, the associative rules defining when close proximity of the primary object and at least two other objects to each another is likely to result in transfer of the primary object to one of the at least two other objects.

7. The method of claim 1, wherein the primary object is one of a football, a soccer ball, a hockey puck, and a lacrosse ball and the sporting activity is selected from the group consisting of American football, soccer, ice hockey, and lacrosse.

8. The method of claim 7, wherein the secondary objects are players in the sporting activity.

9. An associative tracking apparatus for annotating a delayed feed of a sporting activity with tracking information determined within a tracking apparatus for a plurality of objects, comprising:

a tracking reliability monitor for determining when continuous location tracking information for a primary one of the plurality of objects is not available;

an associative tracker for (a) speculatively associating, when notified by the tracking reliability monitor that continuous location tracking information for the primary object is not available and based upon a highest probability defined within one or more predetermined scenarios of the sporting activity, the primary object with a first one of two secondary ones of the plurality of objects that are proximate a last location of the primary object, (b) when the continuous location tracking information for the primary object becomes available, receiving an updated location for the primary object and evaluating correctness of the speculative association of the primary object with the first secondary object based upon the updated location, to produce a non-speculative association of the primary object with one of the secondary objects; and (c) producing the tracking information with tracking information for the first object, during period when the continuous location tracking information is not available, being based upon tracking information of the non-speculatively associated one of the secondary objects; and an output generator for outputting the tracking information with the delayed feed.

10. The associative tracking apparatus of claim 9, the associative tracker configured to, prior to the step of speculatively associating, non-speculatively associate the primary object with the first secondary object.

11. The associative tracking apparatus of claim 9, the tracking reliability monitor being further configured to determine that continuous location tracking information for the primary object is not available when a data reliability measurement (DRM) for the continuous location tracking information is below a DRM threshold.

12. The associative tracking apparatus of claim 9, wherein the predetermined scenarios of the sporting activity have one or more associative rules that define when close proximity of the primary object with at least two other objects is likely to result in transfer of the primary object to one of the at least two other objects.

13. The associative tracking apparatus of claim 9, wherein the primary object is one of a football, a soccer ball, a hockey puck, and a lacrosse ball and the sporting activity is selected from the group consisting of American football, soccer, ice hockey, and lacrosse.

14. The associative tracking apparatus of claim 13, wherein the secondary objects are players in the sporting activity.

* * * * *

UNITED STATES PATENT AND TRADEMARK OFFICE
CERTIFICATE OF CORRECTION

PATENT NO.         : 10,071,282 B2                                              Page 1 of 1
APPLICATION NO.    : 15/789880
DATED              : September 11, 2018
INVENTOR(S)        : Douglas J. DeAngelis et al.

It is certified that error appears in the above-identified patent and that said Letters Patent is hereby corrected as shown below:

In the Claims

In Claim 1, at Column 18, Lines 22-26:
"outputting the delayed feed with the tracking information for the first object"
Should read:
--outputting the delayed feed with the tracking information for the primary object--

In Claim 5, at Column 18, Lines 49-53:
"the primary object is not available comprising determining a data reliability measurement (DRM)"
Should read:
--the primary object is not available comprising determining a data reliability metric (DRM)--

In Claim 9, at Column 19, Lines 26-28:
"(c) producing the tracking information with tracking information for the first object"
Should read:
--(c) producing the tracking information with tracking information for the primary object--

In Claim 11, at Column 20, Lines 11-13:
"continuous location tracking information for the primary object is not available when a data reliability measurement (DRM)"
Should read:
--continuous location tracking information for the primary object is not available when a data reliability metric (DRM)--

Signed and Sealed this
Thirteenth Day of August, 2019

Andrei Iancu
*Director of the United States Patent and Trademark Office*